US008672957B2

(12) United States Patent
Kimhi et al.

(10) Patent No.: US 8,672,957 B2
(45) Date of Patent: Mar. 18, 2014

(54) ADHESIVE PATCH VASCULAR APPLICATOR

(75) Inventors: Ohad Kimhi, Kiryat Yam (IL); Dudu Haimovich, Ramat Ishai (IL); Aviad Louzon, Haifa (IL)

(73) Assignee: SEAlantis Ltd., Haifa (IL)

( * ) Notice: Subject to any disclaimer, the term of this patent is extended or adjusted under 35 U.S.C. 154(b) by 51 days.

(21) Appl. No.: 13/192,627

(22) Filed: Jul. 28, 2011

(65) Prior Publication Data

US 2013/0030453 A1 Jan. 31, 2013

(51) Int. Cl.
*A61B 17/11* (2006.01)

(52) U.S. Cl.
USPC ........................................ 606/153

(58) Field of Classification Search
USPC .................. 606/153, 151, 205–211, 213
See application file for complete search history.

(56) References Cited

U.S. PATENT DOCUMENTS

| | | | |
|---|---|---|---|
| 1,881,383 A | 10/1932 | Wylie | |
| 1,992,344 A | 2/1935 | Alhadate | |
| 2,715,903 A | 8/1955 | Scholl | |
| 3,358,682 A | 12/1967 | Preston | |
| 3,542,021 A | 11/1970 | Preston | |
| 4,230,119 A | 10/1980 | Blum | |
| 4,374,520 A | 2/1983 | Grossmann et al. | |
| 4,840,187 A | 6/1989 | Brazier | |
| 5,024,217 A | 6/1991 | Spencer | |
| 5,151,102 A | 9/1992 | Kamiyama et al. | |
| 5,259,835 A | 11/1993 | Clark et al. | |
| 5,368,581 A | 11/1994 | Smith et al. | |
| 6,508,430 B1 | 1/2003 | Rodriguez | |
| 6,695,515 B1 | 2/2004 | Fleury | |
| 2002/0026159 A1 | 2/2002 | Zhu et al. | |
| 2002/0052570 A1 | 5/2002 | Naimer | |
| 2002/0115952 A1 | 8/2002 | Johnson et al. | |
| 2003/0225422 A1 | 12/2003 | Mosnier et al. | |
| 2004/0138601 A1 | 7/2004 | Chalmers | |
| 2004/0238559 A1 | 12/2004 | Ross | |
| 2005/0125013 A1 | 6/2005 | Kessler | |

(Continued)

FOREIGN PATENT DOCUMENTS

| | | |
|---|---|---|
| GB | 2 211 740 A | 7/1989 |
| GB | 2 235 134 A | 2/1991 |

(Continued)

OTHER PUBLICATIONS

"Medical Instruments/Equipment Catalogue", The FDRE Ministry of Health Pharmaceuticals Fund and Supply Agency, Ethiopia, Dec. 2008, 4 pages.

(Continued)

*Primary Examiner* — Julian W Woo
*Assistant Examiner* — Shaun L David
(74) *Attorney, Agent, or Firm* — Ladas & Parry LLP

(57) ABSTRACT

Apparatus is provided for applying one or more patches to a tubular structure in a body of a patient. The apparatus includes an applicator, which is configured to removably hold the one or more patches, and to place the one or more patches at least partially around the tubular structure. The applicator includes one or more patch supports. Each of the patch supports includes a yielding pad, which is removably coupleable to one of the patches; and a stiff back support structure, to which the yielding pad is fixed. Each of the patch supports is shaped so as to define at least one chamber that itself has a volume of at least 0.5 ml when the patch supports are in respective resting states. Other embodiments are also described.

34 Claims, 12 Drawing Sheets

(56) References Cited

U.S. PATENT DOCUMENTS

| | | |
|---|---|---|
| 2005/0153090 A1 | 7/2005 | Marchitto et al. |
| 2005/0274453 A1 | 12/2005 | Anvar |
| 2006/0085031 A1 | 4/2006 | Bettuchi |
| 2007/0068837 A1 | 3/2007 | D'Angelis |
| 2008/0114466 A1 | 5/2008 | Shelton |
| 2008/0167400 A1 | 7/2008 | Bianco-Peled et al. |
| 2008/0167680 A1 | 7/2008 | Voegele et al. |
| 2012/0078293 A1 | 3/2012 | Hassidov et al. |

FOREIGN PATENT DOCUMENTS

| | | |
|---|---|---|
| GB | 2 457 870 A | 9/2009 |
| JP | 2001-309985 A | 11/2001 |
| JP | 2004-337580 A | 12/2004 |
| WO | 84/01285 A1 | 4/1984 |
| WO | 2006/044799 A2 | 4/2006 |
| WO | 2006/092798 A2 | 9/2006 |
| WO | 2009/060438 A2 | 5/2009 |
| WO | 2009/060439 A2 | 5/2009 |
| WO | 2010/109471 A1 | 9/2010 |
| WO | 2010/140146 A2 | 12/2010 |
| WO | 2010/146582 A2 | 12/2010 |

OTHER PUBLICATIONS

International Search Report and Written Opinion dated Jul. 20, 2010 issued during prosecution of PCT/IL2010/000268.
International Preliminary Report on Patentability dated Jul. 20, 2010 issued during prosecution of PCT/IL2010/000268.
European Search Report dated Dec. 14, 2011; Application No. 11175860.3-1269.
An Examination Report dated Jan. 23, 2013, which issued during the prosecution of Australian Patent Application No. 2012203958.

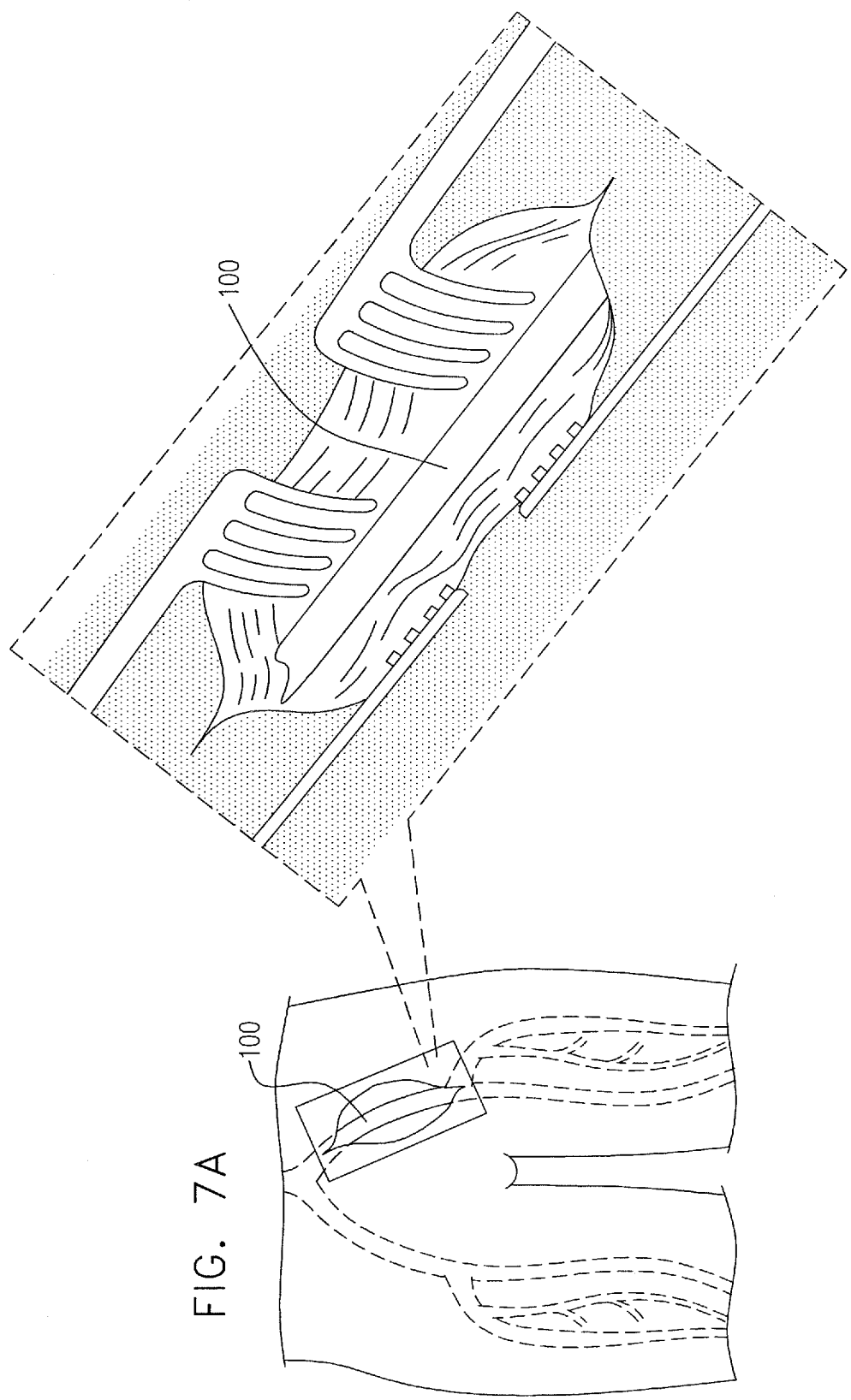

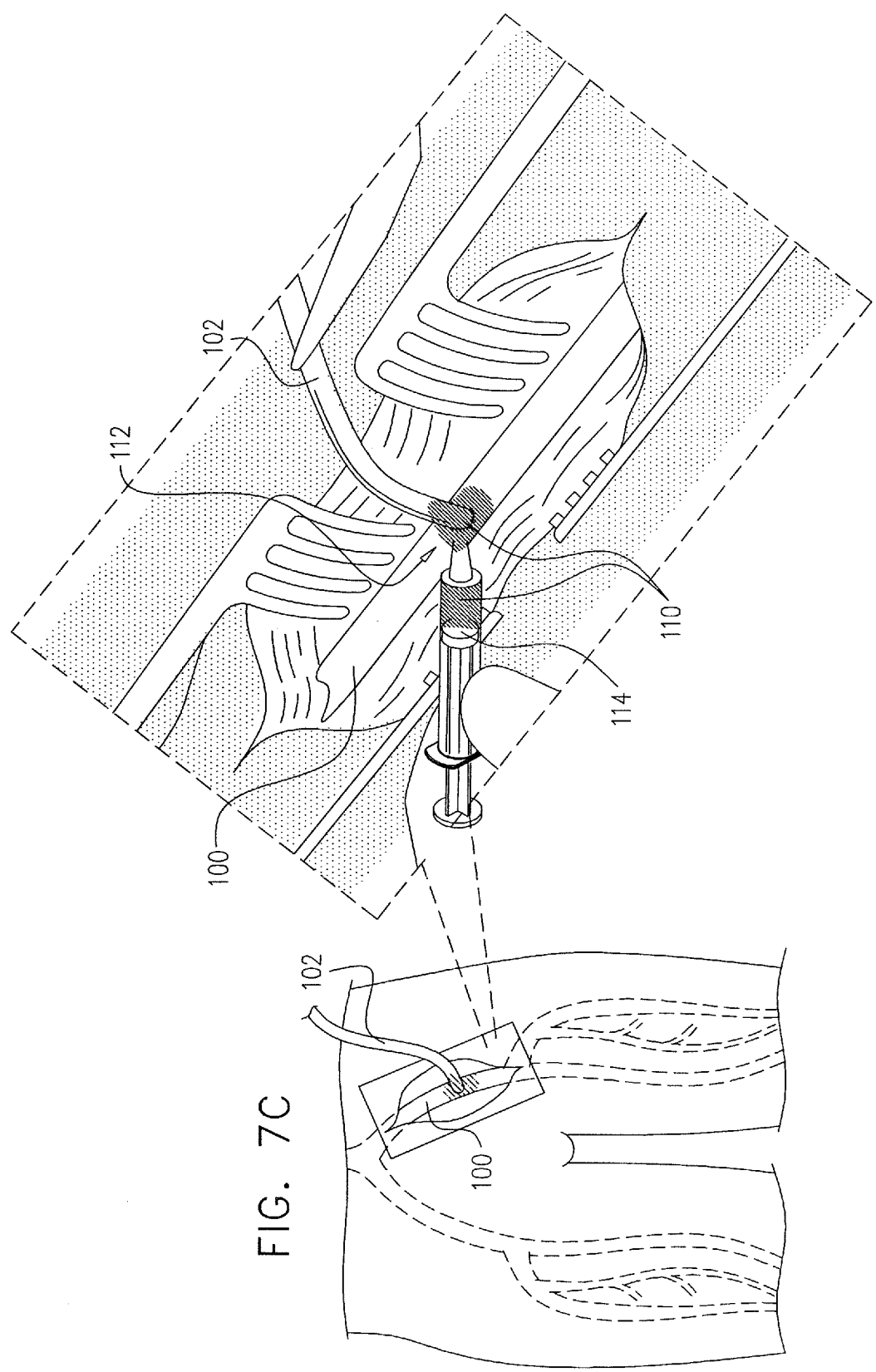

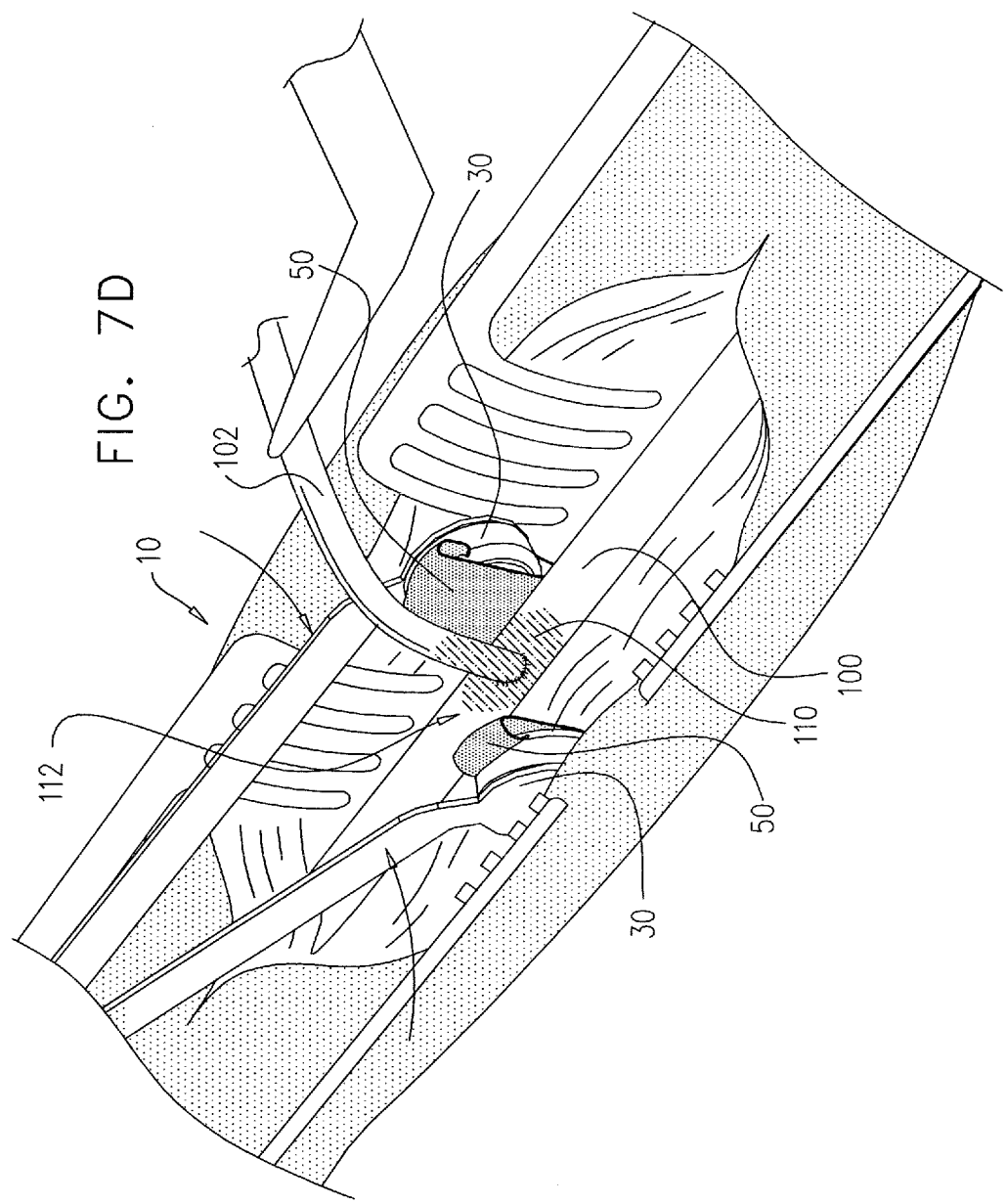

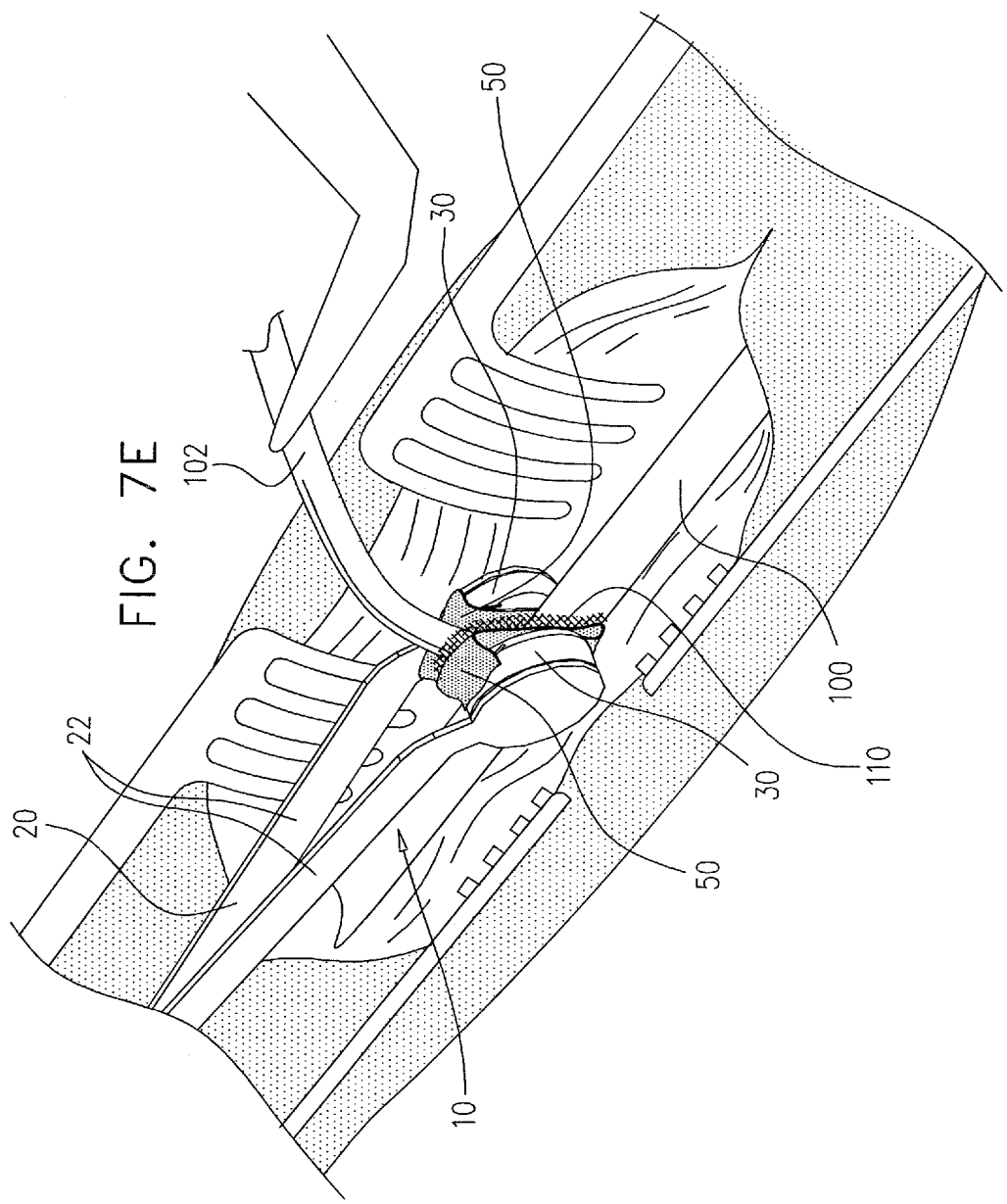

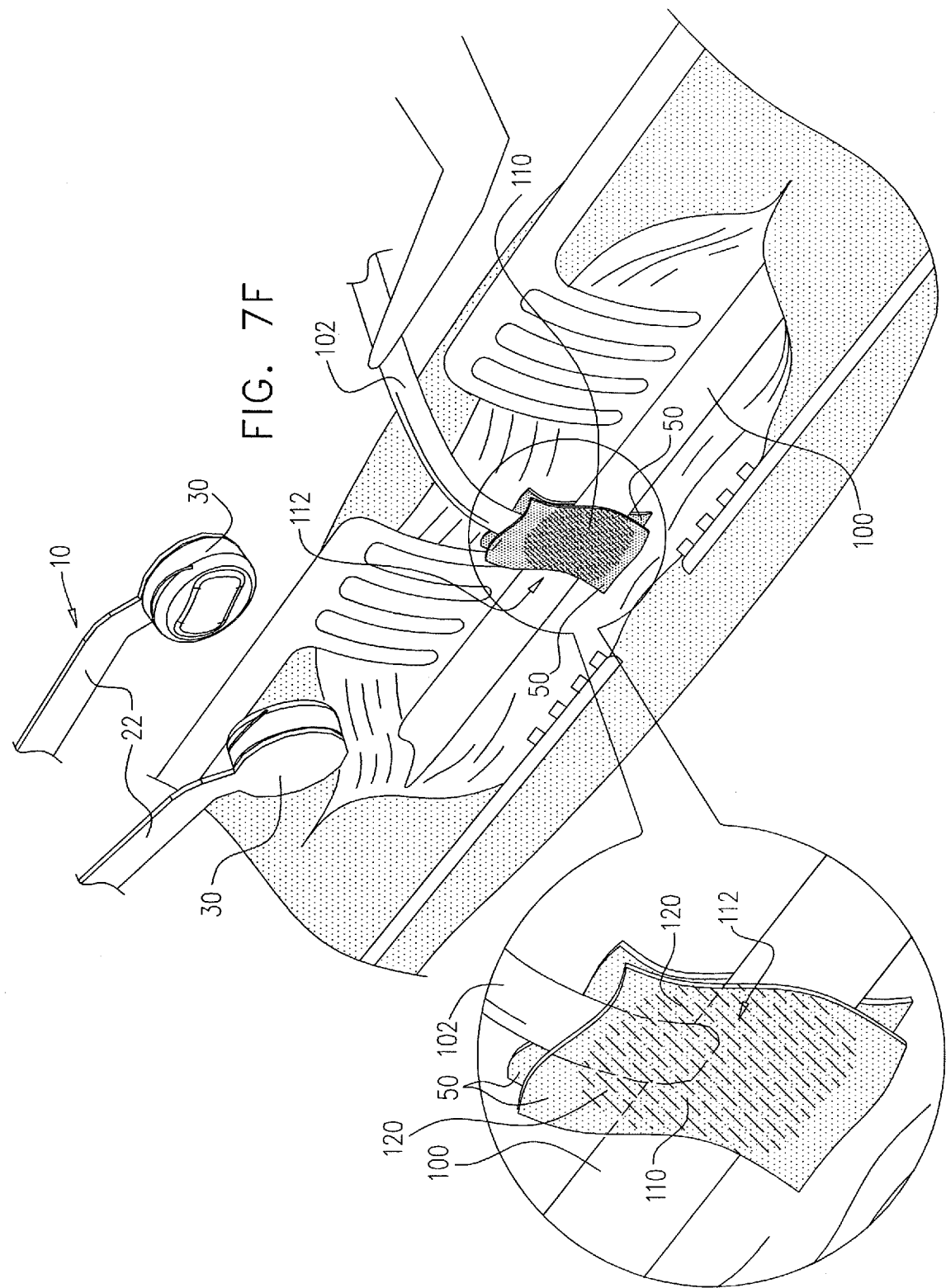

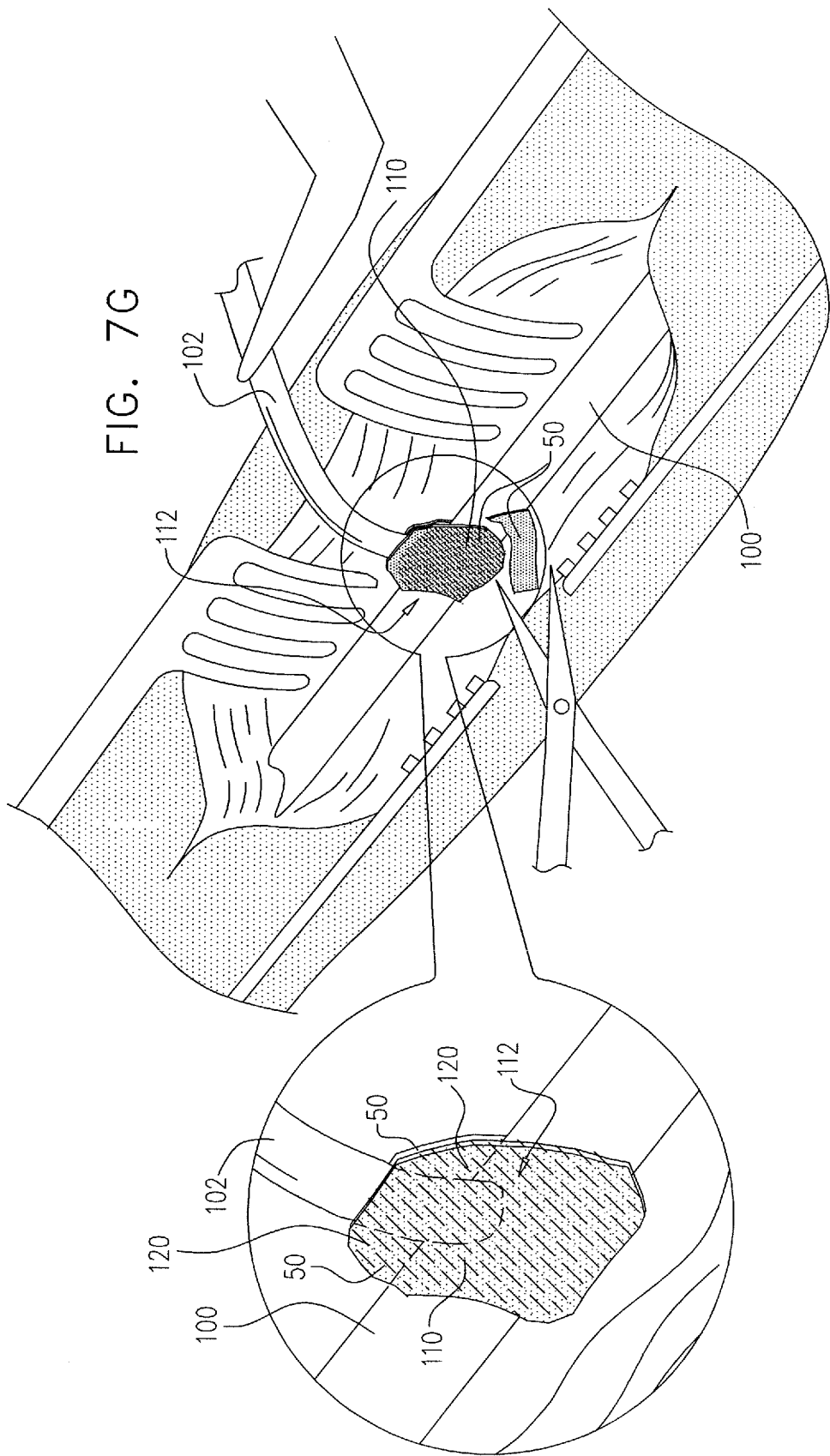

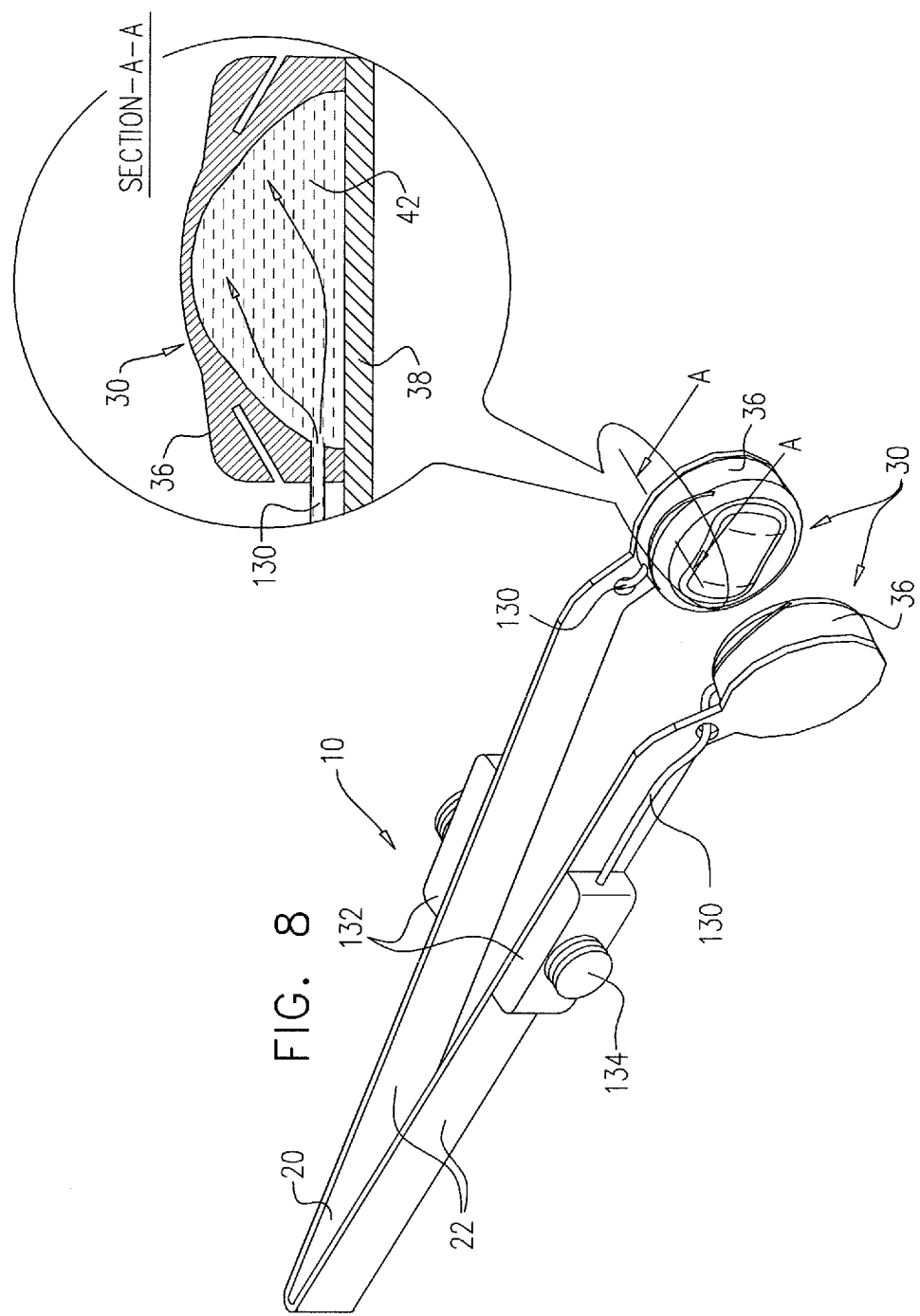

ADHESIVE PATCH VASCULAR APPLICATOR

FIELD OF THE APPLICATION

The present invention relates to an applicator system for applying adhesives or sealants compound to tissues and other structures in vivo.

BACKGROUND OF THE APPLICATION

Tissue adhesives have been increasingly used to enhance traditional closure technologies such as sutures and staples, offering improved sealing capabilities, plugging of undesired leaks, and quicker achievement of hemostasis. Using an adhesive for tissue reattachments or repair procedures usually requires the drying of the tissue surface. The method of applying the adhesive materials influences the effectiveness of the adhesive.

PCT Publication WO 10/109471 to Hassidov et al., which is incorporated herein by reference, describes apparatus for use with a tubular structure in a body of a patient. The apparatus includes an adhesive including first and second components, a container, one or more patches, and an applicator. The container contains the first component of the adhesive and not the second component of the adhesive. The one or more patches include the second component of the adhesive and not the first component of the adhesive. The applicator is configured to removably hold the one or more patches, and to place the one or more patches at least partially around the tubular structure.

PCT Publication WO 06/092798 to Bianco-Peled et al. and US Patent Application Publication 2008/0167400, which are incorporated herein by reference, describe a novel composition-of-matter, method of manufacturing thereof, and applications thereof as an adhesive, in a wide variety of different fields, and in particular, in the health care fields of medicine, dentistry, and veterinary science. The techniques are for use by health care providers, such as medical, dental, and veterinary, surgeons, in procedures for reattaching or repairing body parts or components thereof, such as tissue, of (human or animal) subjects, especially under wet conditions, for example, involving adhesion of wet surfaces. The composition comprises a cross-linked form of a water miscible polymer, and at least one phloroglucinol type compound selected from the group consisting of: phloroglucinol, a derivative of phloroglucinol, and a polymer synthetically prepared from phloroglucinol or a derivative of phloroglucinol. An exemplary water miscible polymer is a naturally existing, or synthetically prepared, salt form of the carbohydrate alginic acid, such as sodium alginate, or alginic acid itself.

PCT Publication WO 09/060438 to Bianco-Peled et al., which is incorporated herein by reference, describes an adhering bandage, especially used for medical purposes, that comprises pre-gel of phenol-based compound and water miscible polymer that is capable of interacting with a cross linking agent. This mixture is provided with a solid support to form a bandage. An in-situ method of applying adhering bandage is also described.

PCT Publication WO 09/060439 to Bianco-Peled et al., which is incorporated herein by reference, describes a composition of matter for to be used as an adhesive that comprises pre-gel made of phenol-based compound and water miscible polymer that interacts with a cross linking agent. A method of in-situ applying the adhesive is also described.

SUMMARY OF THE APPLICATION

Some embodiments of the present invention provide an adhesive patch vascular applicator for applying patches to a tissue surface, such as to a tubular tissue structure in a body of patient. The applicator is configured to removably hold the patches, and to place the patches at least partially around the tubular structure. The applicator comprises one or more (typically, exactly two) patch supports. Each of the patch supports comprises a yielding pad and a stiff back support structure, to which the yielding pad is fixed. For some applications, each of the patch supports is shaped so as to define one or more chambers, such as exactly one chamber. The chambers may provide pliable cushioning to the yielding pad, enabling the yielding pad to adapt to the uneven shape of the tubular structure to which it is applied. Typically, at least one of the chambers itself has a volume of at least 0.5 ml when the patch support is in its resting state.

For some applications, the applicator comprises a forceps. The patch supports are typically coupled to respective arms of the forceps at respective distal ends of the arms. The arms and patch supports are configured such that front surfaces of the yielding pads face each other. Squeezing the arms together brings the front surfaces closer together.

For some applications, a side surface of each yielding pad is shaped so as to define one or more slits, which are configured to removably couple one of the patches to the yielding pad. The side surface may be shaped so as to define two or more slits, such as exactly two slits, which are typically located on opposite sides of the yielding pad. The yielding pad is shaped such that pressing the front surface against an object, such as a tubular structure, opens the slits, thereby automatically releasing the patch from the yielding pad. Although not necessary for allowing the opening of slits, the one or more chambers generally help facilitate such opening, by allowing a central portion of the front surface of the yielding pad to move toward back support structure, thereby lifting the front edges of the yielding pad on both sides of the yielding pad and opening the slits.

For some applications, each of the yielding pads is shaped such that a central portion of the front surface defines a protrusion that protrudes from the front surface in a direction away from the back support structure, at least when the yielding pad is in its resting state. The protrusion may serve to focus pressure applied by yielding pad to the tubular structure, and to push the patch around the tubular structure. For applications in which the patch comprises an adhesive curing agent, such as described hereinbelow, such pushing may help deliver the curing agent to the tubular structure and into good contact with a first component of an adhesive previously applied to the tubular structure, such as described hereinbelow.

In some applications of the present invention, the methods and applicators described herein are used for applying patches and/or substances as an adjunct to suturing. For some applications, a first substance is applied to one or more tubular structure, such as blood vessels and/or synthetic grafts. The applicator is subsequently used to apply one or more patches to the tubular structure(s). For some applications, the patches comprise a second substance, which, upon application of the patches to the tubular structure(s), is brought into contact with the first substance and the tubular structure(s). The applicator typically also helps evenly spread the first substance on the tubular structure(s).

For some applications, the first substance comprises a first component of an adhesive (i.e., a glue or sealant), such as a viscous pre-gel. For some applications, the second substance comprises a second component of the adhesive, typically an adhesive curing agent, which may comprise a gel, liquid, solid, spray, or aerosol, which may be applied to one or more surfaces of the patches and/or be absorbed into the patches.

Upon contact with the first component of the adhesive, the curing agent causes the glue to become more solid, such as a flexible solid gel, and to adhere to the tubular structure. The patch also provides mechanical support to the tubular structure. The patch is typically left on the tubular structure, and eventually biodegrades.

As mentioned above, the applicators and techniques described herein are typically used during a procedure for applying the adhesive and patch to a tubular structure, e.g., a blood vessel, such as an artery, vein, and/or a synthetic graft. For some applications, patches and/or the components of the adhesive are applied to an junction between two tubular structures, such as two tubular body parts, e.g., at a site of an anastomosis between two blood vessels. The junction may, for example, be an end-to-end junction or an end-to-side junction. Alternatively, the methods and applicators are used to apply patches and/or the components of the adhesive to another structure, such as, but not limited to, anatomical structures, such as the gastrointestinal tract (e.g., the colon), a bronchus, or the brain (such as the dura mater), or a synthetic structure within a body of a patient, such as a synthetic graft (e.g., a tubular synthetic graft). Typically, but not necessarily, the structure is tubular.

The methods and applicators of embodiments of the present invention enable quick and accurate application of the patches to the entire tissue surface. Such quick and accurate application is important because the first component of the adhesive generally cures quickly upon contact with the curing agent. The techniques described herein can be used to apply adhesives to hydrated tissue surfaces, without requiring the tissue surfaces to first be dried. In addition, the techniques described herein are generally effective for patients who receive anticoagulation for the procedure, as is common for vascular surgery.

There is therefore provided, in accordance with an application of the present invention, apparatus for applying one or more patches to a tubular structure in a body of a patient, the apparatus including an applicator, which is configured to removably hold the one or more patches, and to place the one or more patches at least partially around the tubular structure, which applicator includes one or more patch supports, each of which includes:

a yielding pad, which is removably coupleable to one of the patches; and a stiff back support structure, to which the yielding pad is fixed, wherein each of the patch supports is shaped so as to define at least one chamber that itself has a volume of at least 0.5 ml when the patch supports are in respective resting states.

For some applications, each of the patch supports is shaped so as to define the at least one chamber thereof between the yielding pad thereof and the back support structure thereof. Alternatively, for some applications, each of the patch supports is shaped so as to define the at least one chamber thereof entirely within the yielding pad thereof.

For some applications, the yielding pad of each of the patch supports is shaped so as to define: a front surface that faces away from the back support structure thereof, and a side surface between the front surface and the back support structure thereof, which side surface is shaped so as to define one or more slits, which are configured to removably couple the one of the patches to the yielding pad. For some applications, the yielding pad is shaped such that pressing the front surface against the tubular structure opens the slits, thereby releasing the one of the patches from the yielding pad. For some applications, the side surface is shaped so as to define two or more slits, such as exactly two slits on opposite sides of the yielding pad. For some applications, at least one of the slits is arcuate at least when in a closed position. For some applications, ends of the at least one of the slits are closer to the front surface than to the back support structure, at least when the at least one of the slits is in the closed position.

For any of the applications described above, the yielding pad of each of the patch supports may be shaped so as to define a front surface that faces away from the back support structure thereof, and such that a central portion of the front surface defines a protrusion that protrudes from the front surface in a direction away from the back support structure, at least when no force is applied to the front surface. For some applications, the yielding pad is shaped such that the central portion of the front surface, but not the entire front surface, defines the protrusion.

For any of the applications described above, the applicator may include a forceps, which includes exactly two arms; the one or more patch supports may include exactly two patch supports, which are coupled to the two arms, respectively; the patch supports may include exactly two yielding pads, respectively; the arms and the patch supports may be configured such that front surfaces defined by the yielding pads, respectively, face each other; and the arms may be sufficiently flexible to limit a maximum amount of force applied by the patch supports to the tubular structure when the patch supports are placed on opposing sides of the tubular structure and the arms are squeezed together.

For any of the applications described above, the yielding pad of each of the patch supports may be shaped so as to define a front surface that faces away from the back support structure thereof, and each of the patch supports may be configured such that, when pressed against the tubular structure, central and peripheral portions of the front surface apply different respective forces to the tubular structure.

For any of the applications described above, the at least one chamber of each of the patch supports may be closed.

For any of the applications described above, an interface between the yielding pad of each of the patch supports and the back support structure thereof may be generally circular.

For any of the applications described above, the yielding pad of each of the patch supports may be shaped so as to define a front surface that faces away from the back support structure thereof, and has a surface area of between 3 and 18 cm2.

For any of the applications described above, the yielding pad of each of the patch supports may be shaped so as to define a front surface that faces away from the back support structure thereof, and a greatest distance between the front surface and the back support structure thereof may be between 4 and 20 mm.

For any of the applications described above, the volume of the at least one chamber of each of the patch supports may be at least 1 ml when the patch supports are in their respective resting states.

For any of the applications described above, the applicator may be configured to place the one or more patches entirely around the tubular structure.

For any of the applications described above, the apparatus may further include the one or more patches. For some applications, the one or more patches include mesh. For some applications, the one or more patches include an adhesive curing agent. For some applications, the adhesive curing agent is a first component of a two-component adhesive, and the apparatus further includes a container, which contains a second component of the adhesive. For some applications, the second component of the adhesive includes a pre-gel.

For any of the applications described above, each of the patch supports may further include a gas that fills the at least one chamber. Alternatively, for any of the applications described above, each of the patch supports may further include a gel that fills the at least one chamber.

For any of the applications described above, the yielding pad of each of the patch supports may include a soft polymer. For example, the soft polymer may include silicone. For some applications, the silicone has a hardness of between 5 and 60 Shore A.

For any of the applications described above, at least one of the patch supports may be shaped so as to define exactly one chamber. Alternatively, for any of the applications described above, at least one of the patch supports may be shaped so as to define a plurality of chambers, each of which has a volume of at least 0.5 ml.

For any of the applications described above, the tubular structure may be a tubular body part.

For any of the applications described above, the tubular structure may be one or more structures selected from the group consisting of: at least one blood vessel, and at least one synthetic graft.

For any of the applications described above, the applicator may be configured to place the one or more patches at least partially around the tubular structure having a diameter of between 2 and 30 mm.

There is further provided, in accordance with an application of the present invention, apparatus for applying one or more patches to a tubular structure in a body of a patient, the apparatus including an applicator, which is configured to removably hold the one or more patches, and to place the one or more patches at least partially around the tubular structure, which applicator includes one or more patch supports, each of which includes:

a stiff back support structure; and a yielding pad, which is fixed to the back support structure, and which is shaped so as to define:

a front surface that faces away from the back support structure, and a side surface between the front surface and the back support structure, which side surface is shaped so as to define one or more slits, which are configured to removably couple the one of the patches to the yielding pad.

For some applications, the yielding pad is shaped such that pressing the front surface against the tubular structure opens the slits, thereby releasing the one of the patches from the yielding pad.

For some applications, the side surface is shaped so as to define two or more slits, such as exactly two slits on opposite sides of the yielding pad.

For some applications, at least one of the slits is arcuate at least when in a closed position. For some applications, ends of the at least one of the slits are closer to the front surface than to the back support structure, at least when the at least one of the slits is in the closed position.

For some applications, the yielding pad of each of the patch supports is shaped so as to define a front surface that faces away from the back support structure thereof, and such that a central portion of the front surface defines a protrusion that protrudes from the front surface in a direction away from the back support structure, at least when no force is applied to the front surface. For some applications, the yielding pad is shaped such that the central portion of the front surface, but not the entire front surface, defines the protrusion.

For some applications, the applicator includes a forceps, which includes exactly two arms.

For any of the applications described above, the apparatus may further include the one or more patches. For some applications, the one or more patches include an adhesive curing agent.

There is still further provided, in accordance with an application of the present invention, a method for applying one or more patches to a tubular structure in a body of a patient, the method including:

providing an applicator that includes one or more patch supports, each of which includes (a) a yielding pad, to which one of the patches is removably coupled, and (b) a stiff back support structure, to which the yielding pad is fixed, wherein each of the patch supports is shaped so as to define at least one chamber that itself has a volume of at least 0.5 ml when the patch supports are in their respective resting states; and placing the one or more patches at least partially around the tubular structure, by using the applicator to press the one or more patch supports against the tubular structure.

For some applications:

providing the applicator includes providing the applicator in which the yielding pad of each of the patch supports is shaped so as to define (a) a front surface that faces away from the back support structure thereof, and (b) a side surface between the front surface and the back support structure thereof, which side surface is shaped so as to define one or more slits, which are configured to removably couple the one of the patches to the yielding pad, and placing includes pressing the front surface against the tubular structure so as to open the slits, thereby releasing the one of the patches from the yielding pad.

For any of the applications described above, the method may further include, after placing, releasing the one or more patches from the patch supports.

For any of the applications described above, placing may include placing the one or more patches entirely around the tubular structure.

For any of the applications described above, the tubular structure may be a tubular body part. For any of the applications described above, the tubular structure may be one or more structures selected from the group consisting of: at least one blood vessel, and at least one synthetic graft.

For any of the applications described above, the tubular structure may be a blood vessel to which a structure has been anastomosed at an anastomosis site, the structure selected from the group selected from: a synthetic graft and a second blood vessel, and placing may include placing the one or more patches at least partially around the tubular structure and the anastomosis site.

For any of the applications described above, the tubular structure may be a blood vessel upon which an end-to-end anastomosis has been performed at an anastomosis site, and placing may include placing the one or more patches at least partially around the tubular structure at the anastomosis site.

For any of the applications described above, the method may further include, before placing, applying a first component of an adhesive to the tubular structure, wherein the one or more patches include a second component of the adhesive, and placing may include placing the one or more patches at least partially around the tubular structure, such that the second component of the adhesive comes in contact with the first component of the adhesive. For some applications, the second component of the adhesive includes a curing agent, and placing the one or more patches includes bringing the curing agent into contact with the first component of the adhesive. For some applications, the first component of the adhesive includes a pre-gel, and applying the first component includes applying the pre-gel to the tubular structure.

There is additionally provided, in accordance with an application of the present invention, a method for applying one or more patches to a tubular structure in a body of a patient, the method including:

providing an applicator that includes one or more patch supports, each of which includes (a) a stiff back support structure, and (b) a yielding pad, which is fixed to the back support structure, and which is shaped so as to define (i) a front surface that faces away from the back support structure, and (ii) a side surface between the front surface and the back support structure, which side surface is shaped so as to define one or more slits, which are configured to removably couple the one of the patches to the yielding pad; and placing the one or more patches at least partially around the tubular structure, by using the applicator to press the one or more patch supports against the tubular structure, so as to open the slits, thereby releasing the one of the patches from the yielding pad.

For some applications, placing includes placing the one or more patches entirely around the tubular structure.

For some applications, the tubular structure is a tubular body part. For some applications, the tubular structure is one or more structures selected from the group consisting of: at least one blood vessel, and at least one synthetic graft.

For some applications, the tubular structure is a blood vessel to which a structure has been anastomosed at an anastomosis site, the structure selected from the group selected from: a synthetic graft and a second blood vessel, and placing includes placing the one or more patches at least partially around the tubular structure and the anastomosis site.

For some applications, the tubular structure is a blood vessel upon which an end-to-end anastomosis has been performed at an anastomosis site, and placing includes placing the one or more patches at least partially around the tubular structure at the anastomosis site.

For some applications, the method further includes, before placing, applying a first component of an adhesive to the tubular structure, the one or more patches include a second component of the adhesive, and placing includes placing the one or more patches at least partially around the tubular structure, such that the second component of the adhesive comes in contact with the first component of the adhesive.

The present invention will be more fully understood from the following detailed description of embodiments thereof, taken together with the drawings, in which:

BRIEF DESCRIPTION OF THE DRAWINGS

FIGS. 7A-G are schematic illustrations of an end-to-side anastomosis procedure, performed in accordance with an application of the present invention;

FIG. 8 is a schematic illustration of an alternative configuration of the applicator of FIG. 1, in accordance with an application of the present invention.

DETAILED DESCRIPTION OF APPLICATIONS

Figure 1:
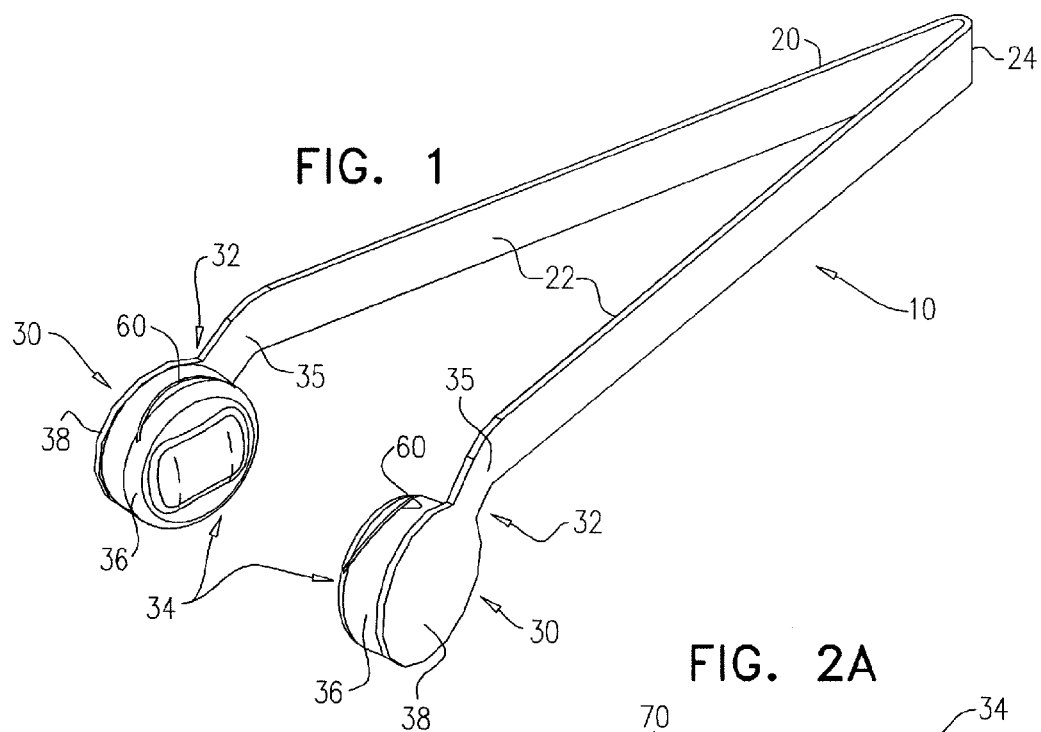
FIG. 1 is a schematic illustration of an adhesive patch vascular applicator, in accordance with an application of the present invention.

FIG. 1 is a schematic illustration of an adhesive patch vascular applicator 10, in accordance with an application of the present invention. Vascular applicator 10 is configured to removably hold the one or more patches, and to place the one or more patches at least partially around a tubular structure in a body of a patient. For some applications, applicator 10 comprises a forceps 20, which comprises exactly two arms 22, which are typically spring-connected at a proximal end 24, such as in conventional tweezers. The arms define a space therebetween which is reduced and increased as the arms are moved toward and away from each other, respectively. Alternatively, for some applications, the arms are coupled to each another by a hinge, and shaped so as to define respective handles 10 and 11, such as described in above-mentioned PCT Publication WO 10/109471 to Hassidov et al., for example with reference to FIGS. 1A-F thereof.

Applicator 10 further comprises one or more (typically, exactly two) patch supports 30. Patch supports 30 are typically coupled to respective arms 22 at respective distal ends 32 of the arms. Patch supports comprise respective yielding pads 36, which define respective front surfaces 34. Arms 22 and patch supports 30 are configured such that front surfaces 34 face each other. Squeezing the arms together brings front surfaces 34 closer together. The surgeon may use his or her thumb and index finger to apply pressure near the longitudinal center of each arm.

For some applications, arms 22 comprise stainless steel approved for medical use, such as SS302, or plastic. Forceps 20 may be provided with arms having a plurality of sizes appropriate for surgeons with hands of different sizes. Typically, each of arms 22 has a length of at least 10 cm, no more than 25 cm, and/or between 10 and 25 cm, such as 15 cm, and a thickness of at least 1 mm, no more than 3 mm, and/or between 1 and 3 mm, such as 1.2 mm. Optionally, each arm 22 has a bent portion 35 near its distal end 32, such as in order to allow direct access to a blood vessels and/or an anastomosis even at a depth of a few centimeters. Forceps 20 is typically shaped to allow use by both right and left hands. Typically, forceps 20 does not comprise a locking mechanism.

For some applications, rather than comprising forceps 20, applicator 10 comprises a single arm and single patch support 30 (configuration not shown). For example, such a configuration may be useful for treating cuts in arteries, such as made during endarterectomy.

For some applications, applicator 10 is single-use or semi-disposable. Alternatively, applicator 10 is configured to be reusable.

Figure 2A:
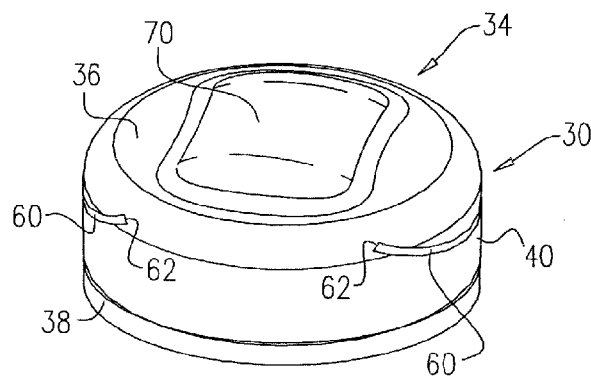
FIGS. 2A-B are schematic illustrations of one of the patch supports of the applicator of FIG. 1, in accordance with an application of the present invention.
Figure 2B:
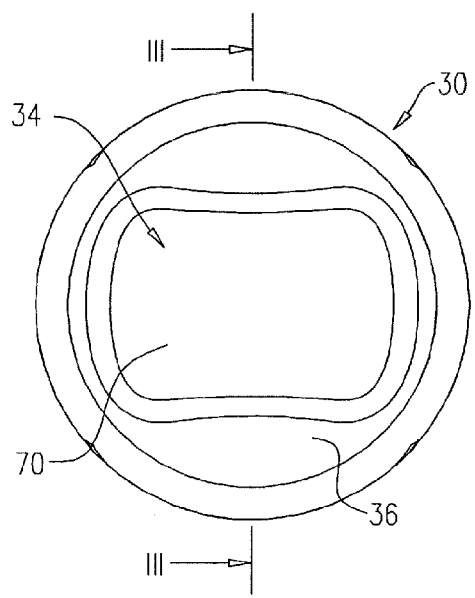
Figure 3:
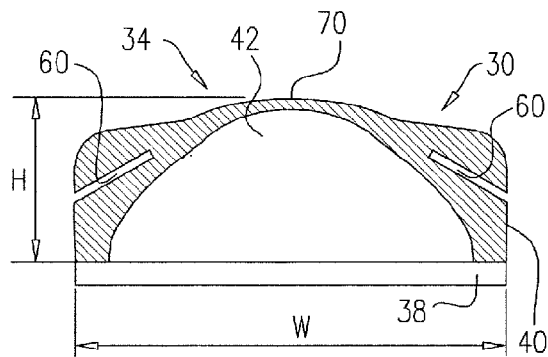
FIG. 3 is a schematic cross-sectional illustration of one of the patch supports of the applicator of FIG. 1, in accordance with an application of the present invention.

Reference is still made to FIG. 1, and is additionally made to FIGS. 2A-B, which are schematic illustrations of one of patch supports 30, and to FIG. 3, which is a schematic cross-sectional illustration of one of patch supports 30, in accordance with an application of the present invention. Each of patch supports 30 comprises one of yielding pads 36 and a stiff back support structure 38, to which the yielding pad is fixed, e.g., using a medical-grade silicone adhesive (e.g., ELASTOSIL® E41, Wacker Chemie AG, Munich, Germany). Back support structure 38 is typically shaped as a flat plate. Back support structure 38 and arm 22 may be formed of a single piece (as shown), or may be formed of separate pieces that are fixed together (not shown). For some applications, as shown in the figures, an interface between yielding pad 36 and back support structure 38 is generally circular, and back support structure 38 is generally circular. Alternatively, the interface has another shape, such as an ellipse or rectangle. For some applications, front surface 34 of each of yielding pads is circular. Alternatively, the front surface may have another shape, such as an ellipse or rectangle, for example for use with specific types of anastomoses.

As mentioned above, each of yielding pads 36 is shaped so as to define front surface 34. Front surface faces away from back support structure 38. For example, front surface 34 may have a surface area of at least 3 cm2, no more than 18 cm2, and/or between 3 and 18 cm2, such as about 5 cm2. In addition, each of yielding pads 36 is typically shaped so as to define a side surface 40 between front surface 34 and back support structure 38 thereof. (It is noted that each of yielding pads 36 defines a single side surface 40 even for applications in which the yielding pads have a shape with more than one edge, such as a rectangle; in such cases, side surface 40 comprises the periphery of the shape.)

Typically, yielding pad 36 of each of patch supports comprises a soft polymer, such as a soft, medical-grade silicone, rubber, a medical-grade pliable foam, or a closed-pore sponge with high void volume. For example, the polymer may have a hardness of at least 5 Shore A, no more than 60 Shore A, and/or between 5 and 60 Shore A, such as 5 Shore A. The polymer optionally comprises a dual-component silicone. Typically, a greatest width W of yielding pad 36 (labeled in FIG. 3), measured parallel to back support structure 38, is at least 10 mm, no more than 50 mm, and/or between 10 and 50 mm, such as 25 mm. (As mentioned above, yielding pad 36 may be circular; in this case, width W corresponds with the diameter of the pad.) These dimensions generally enable the yielding pads to cover even large blood vessels and synthetic vessels, typically having diameters up to 10 mm. Typically, a greatest height H of yielding pad 36 (labeled in FIG. 3), i.e., a greatest distance between front surface 34 and back support structure 38, measured perpendicular to back support structure 38, is at least 4 mm, no more than 20 mm, and/or between 4 and 20 mm, such as 9 mm. These dimensions (height and width) enable the yielding pads to be applied to blood vessels having a large range of diameters and stiffness.

Reference is still made to FIG. 3. For some applications, each of patch supports 30 is shaped so as to define one or more chambers 42, such as exactly one chamber 42. Chambers 42 are typically filled with (a) a gas (typically at atmospheric pressure, or greater than atmospheric pressure), such as zero air; (b) a gel, such as a silicone gel, polymeric gel, and/or a gel having physical or chemical cross-linking; or (c) a liquid. Chambers 42 may provide pliable cushioning to yielding pad 36, enabling the yielding pad to adapt to the uneven shape of the tubular structure(s) to which it is applied. For applications in which chambers 42 are filled with a gas, the gas generally compresses somewhat when chambers 42 are squeezed upon applying the patch support to the tubular structure(s).

When patch support 30 is in its resting state (i.e., no force is applied to the patch support, such as to front surface 34), typically at least one of chambers 42 itself has a volume of at least 0.3 ml, such as at least 0.5 ml, no more than 10 ml, and/or between 0.3 ml or 0.5 ml and 10 ml, such as at least 1 ml or at least 2 ml, no more than 10 ml (e.g., no more than 5 ml), and/or between 1 ml and 5 ml, e.g., about 3 ml (in other words, if more than one of chambers 42 has such a volume, each of the more than one of the chambers, taken separately, has such a volume, rather than all of such chambers in combination having such a volume). Alternatively or additionally, typically at least one of chambers 42 itself has a volume of at least 20%, no more than 80%, and/or between 20% and 80%, such as at least 30%, no more than 50%, and/or between 30% and 50% of the total volume of yielding pad 36, including the chamber, when the yielding pad is in its resting state. For configuration in which patch support 30 is shaped so as to define exactly one chamber 42, single chamber 42 typically has a volume of at least 0.5 ml, no more than 10 ml, and/or between 0.5 ml and 10 ml, such as at least 1 ml or at least 2 ml, no more than 10 ml (e.g., no more than 5 ml), and/or between 1 and 5 ml, e.g., about 3 ml, when the yielding pad is in its resting state. Alternatively or additionally, single chambers 42 typically has a volume of at least 20%, no more than 80%, and/or between 20% and 80%, such as at least 30%, no more than 50%, and/or between 30% and 50% of the total volume of the yielding pad, including the chamber, when the yielding pad is in its resting state.

For some applications, each of chambers 42 is closed, i.e., is sealed such that the gas or gel cannot escape from the chamber. For other applications, chamber 42 has one or more small openings to outside of yielding pad 36, which allow a portion of the gas or gel to escape when pressure is applied to the yielding pad.

For some application, at least one of patch supports 30 is shaped so as to define exactly one chamber 42. For other applications, at least one of patch supports 30 is shaped so as to define a plurality of chambers 42, each of which has a volume of at least 0.5 ml. It is noted that the chambers are substantially larger than the voids (pores) of silicone sponge. In an experiments conducted by the inventors, yielding pads that comprised solid silicone with a chamber did not adapt as well to the shape of tubular structure as did the yielding pads with a chamber described herein.

For some applications, each of patch supports 30 is shaped so as to define the one or more chambers 42 thereof between yielding pad 36 thereof and back support structure 38 thereof, as shown in FIG. 3 (and FIGS. 4A-C, 5, and 6). For other applications, each of patch supports 30 is shaped so as to define chamber 42 thereof entirely within yielding pad 36 thereof (configuration not shown). For some applications in which applicator 10 comprises exactly two patch supports 30, one of the patch supports is shaped so as to define at least one chamber 42, and the other patch support is not shaped so as to define any chambers 42.

Figure 4A:
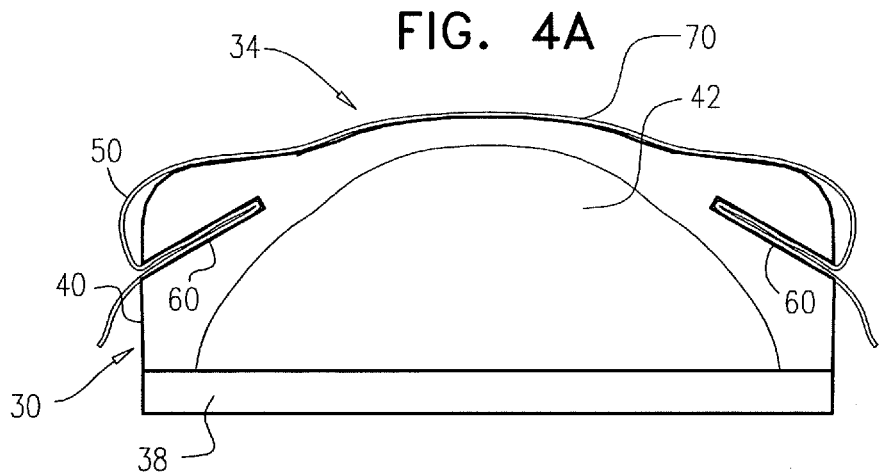
FIGS. 4A-C are schematic cross-sectional illustrations of one of the patch supports of the applicator of FIG. 1 and a patch, in accordance with an application of the present invention.
Figure 4B:
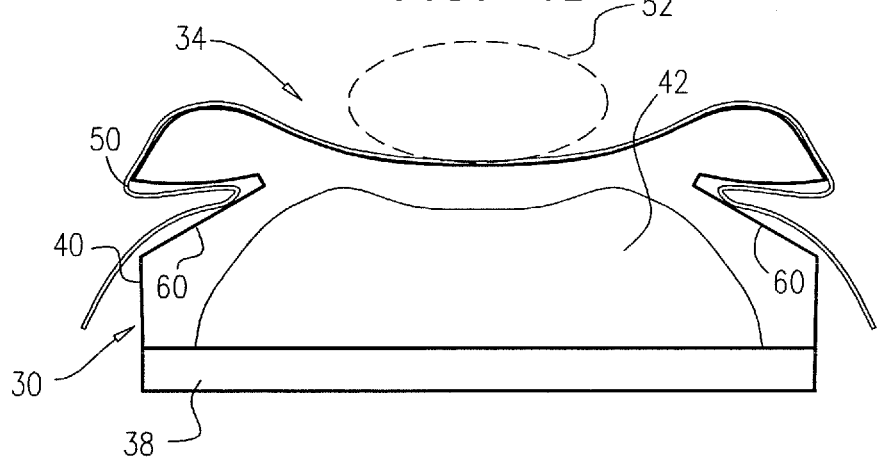
Figure 4C:
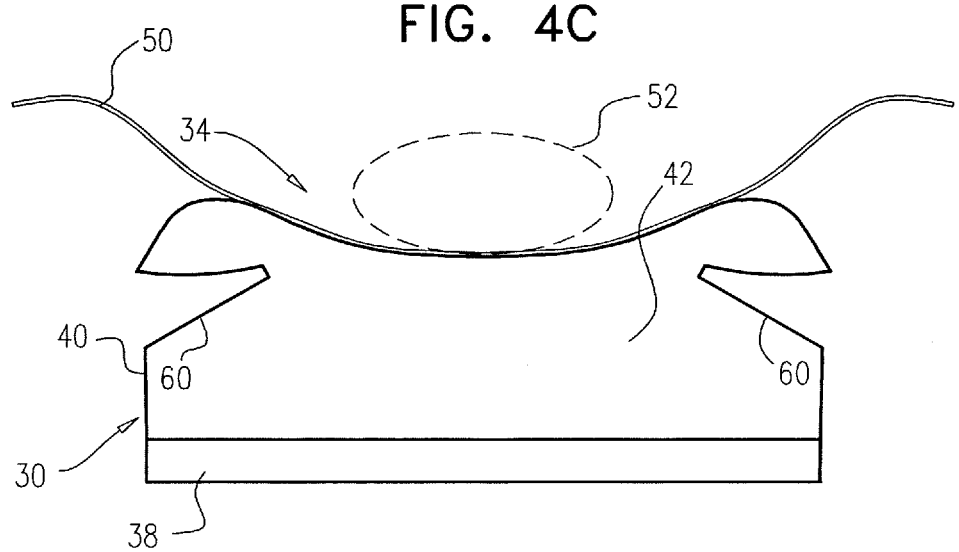

Reference is now made to FIGS. 4A-C, which are schematic cross-sectional illustrations of one of patch supports 30 and a patch 50, in accordance with an application of the present invention. Typically, yielding pad 36 of patch support 30 is removably coupleable to patch 50. Patch 50 typically has an effective area of at least 1 cm2, no more than 40 cm2, and/or between 1 and 40 cm2, such as at least 3 cm2, no more than 15 cm2, and/or between 3 and 15 cm2. For applications in which patch 50 is generally rectangular, the patch typically has dimensions of at least 6 cm×2 cm, no more than 7.5 cm×5 cm, and/or between 6 cm×2 cm and 7.5 cm×5 cm, such as 5 cm×2.5 cm. For some applications, patches 50 are provided by the manufacturer in several sizes, such as small, medium, large, and extra-large, optionally pre-attached to patch supports 30. Alternatively, single-size patches are provided by the manufacturer (e.g., 7.5 cm×7.5 cm), and, during the medical procedure, are cut to size on-site for the particular patient, and are attached to the patch supports. Additional details regarding some configurations of patch 50 are provided hereinbelow.

FIG. 4A shows patch support 30 with patch 50 initially removably coupled thereto. Patch 50 covers at least a portion of (typically all of) front surface 34 of yielding pad 36, and rests against the front surface.

FIG. 4B shows patch 50 partially decoupled from patch support 30. Patch 50 typically comes decoupled automatically when front surface 34 of yielding pad 36 is pressed against an object 52, such as a tubular structure.

FIG. 4C shows the patch entirely decoupled from patch support 30, but still resting against front surface 34 of the yielding pad.

For some applications, as shown in FIGS. 4A-C (and FIGS. 1, 2A, 3, 5, 7D-F, and 8), side surface 40 of each yielding pad 36 is shaped so as to define one or more slits 60, which are configured to removably couple patch to the yielding pad. For some applications, side surface 40 is shaped so as to define two or more slits 60, such as exactly two slits 60, which are typically located on opposite sides of the yielding pad. Typically, yielding pad 36 is shaped such that pressing front surface 34 against object 52, such as a tubular structure, opens slits 60, thereby automatically releasing patch 50 from the yielding pad, such as shown in FIGS. 4B-C. Although not necessary for allowing the opening of slits 60, one or more chambers 42 generally help facilitate such opening, by allowing a central portion of front surface 34 to move toward back support structure 38, thereby lifting the front edges of the yielding pad on both sides of the yielding pad and opening the slits.

For some applications, at least one of slits 60 is arcuate at least when in a closed position, such as can be seen, for example, in FIG. 2A. Typically, ends 62 of the at least one of slits 60 are closer to front surface 34 than to back support structure 38. This shape may help enable release of the patch from the slits. Typically, each of slits 60 has a greatest depth of at least 2 mm, no more than 25 mm, and/or between 2 and 25 mm, such as at least 3 mm, no more than 8 mm, and/or between 3 and 8 mm, e.g., about 4.5 mm. Typically, the depth of each slit varies along the slit. The depth is greatest at about the longitudinal center of the slit, and reaches, or almost reaches, zero at the longitudinal ends of the slit.

For some applications, yielding pad 36 is shaped such that a central portion of front surface 34 defines a protrusion 70 that protrudes from front surface 34 in a direction away from back support structure 38, at least when the yielding pad is in its resting state, i.e., when no force is applied to front surface 34 (for example, before front surface 34 (and patch support 30) is pressed against object 52). Typically, yielding pad 36 is shaped such that the central portion of the front surface, but not the entire front surface, defines the protrusion.

For example, protrusion 70 may be defined by between 0% and 80% of the area of the front surface. Protrusion 70 may have various shapes, such as generally rectangular, optionally with rounded corners, as shown in the figures, or elliptical (e.g., circular). The dimensions of protrusion are typically less than 50×25×15 mm (e.g., 12×17×1.5 mm), and the protrusion may, for example, have a volume of at least 200 mm3, no more than 2000 mm3, and/or between 200 and 2000 mm3.

Protrusion 70 may serve to focus pressure applied by yielding pad 36 to a tubular structure, and to push patch around the tubular structure. For applications in which patch 50 comprises an adhesive curing agent, such pushing may help deliver the curing agent around the tubular structure and into good contact with a first substance applied to the tubular structure, such as described hereinbelow, thus allowing optimal on-site curing of the adhesive. When applicator 10 is used with end-to-side anastomoses, protrusion 70 may help push the patch and curing agent against both the primary and secondary tubular structures in the vicinity of the junction therebetween. Such pushing may be particularly helpful when the diameter of the secondary tubular structure is less than that of the primary tubular structure; without the protrusion, the patch and curing agent may not make good contact with the narrower secondary tubular structure. For some applications, such as for use with end-to-end anastomoses, the applicator is typically configured to place one or more (e.g., two) patches 50 entirely around the tubular structure.

For some applications, each of patch supports 30 is configured such that, when pressed against a tubular structure, central and peripheral portions of front surface 34 apply different respective forces to the tubular structure. For example, these different forces may be caused by chamber 42 and/or protrusion 70, which provide a variable effective hardness across the yielding pad. Typically, the central portion of the front surface applies a greater force than does the peripheral portion. For some applications, yielding pad 36 comprises two or more layers of material (e.g., silicone) having different respective hardnesses. For example, a front layer may be harder than a layer that defines the sides that define the slits.

Figures 5, 6:
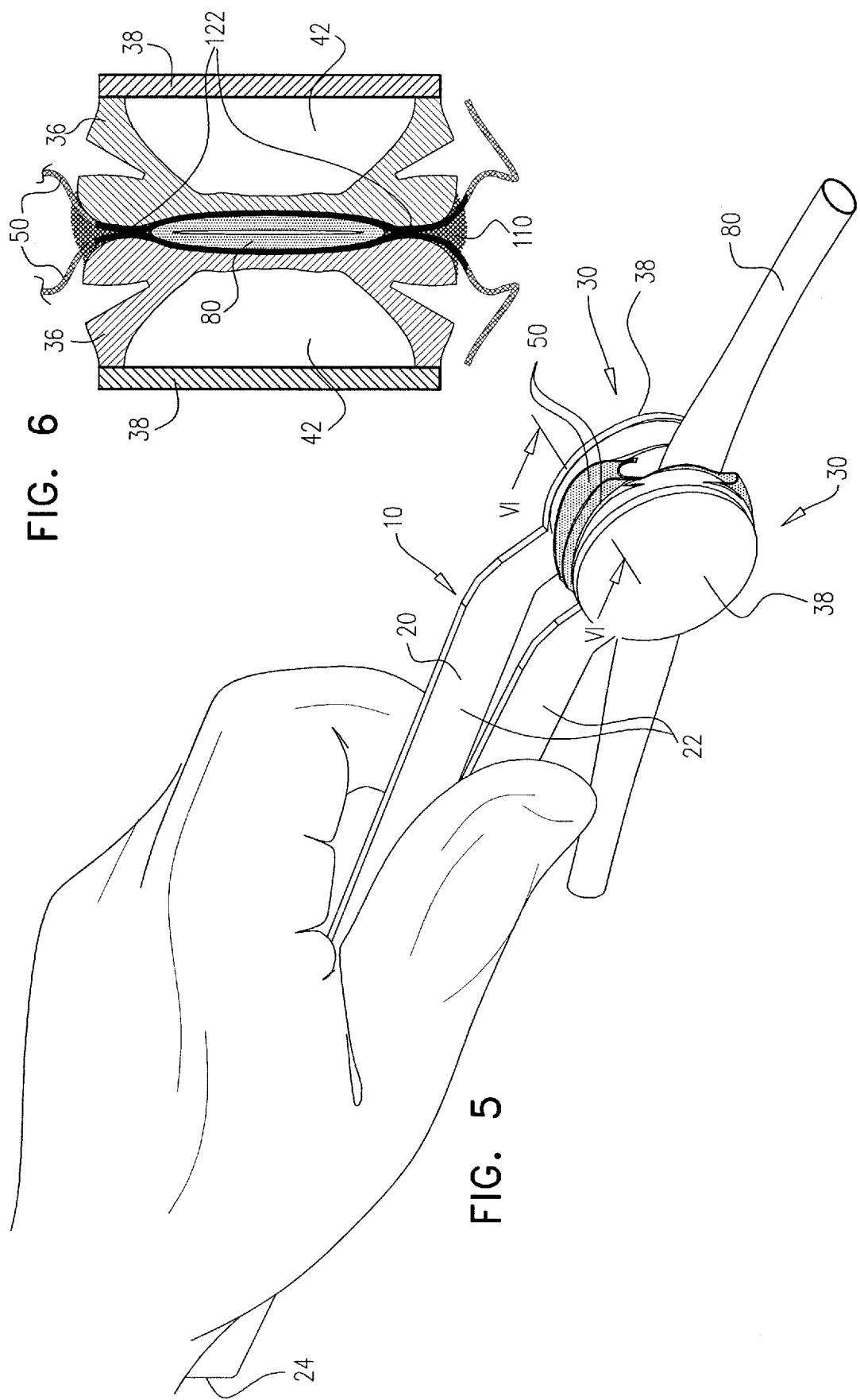
FIG. 5 is a schematic illustration of the use of the applicator of FIG. 1 to apply two patches to a tubular structure, in accordance with an application of the present invention.
FIG. 6 is a cross-sectional view taken along line VI-VI of FIG. 5, in accordance with an application of the present invention.

Reference is now made to FIGS. 5 and 6, which are schematic illustrations of the use of applicator 10 to apply two patches 50 to a tubular structure 80, in accordance with an application of the present invention. FIG. 6 is a cross-sectional view taken along line VI-VI of FIG. 5. The tubular body structure may be a tubular body part, such as a blood vessel, or a synthetic graft, and typically includes an anastomosis. Typically, the tubular structure has a diameter of between 2 and 30 mm. As can be seen in FIGS. 5 and 6, yielding pads 36 are configured to conform with the shape of tubular structure, thereby placing patches 50 in good contact with tubular structure 80.

For some applications, as shown in FIGS. 5 and 6, applicator 10 is used to perform an end-to-end anastomosis procedure. During such an anastomosis procedure, the ends of the blood vessel are first stitched together using conventional techniques, such as using sutures. Optionally, a first component 110 of an adhesive (e.g., a pre-gel) is applied to the blood vessel at the site of the anastomosis. Applicator 10 is used to apply one or more patches 50 at least partially around, such as entirely around the blood vessel. Typically, in such end-to-end anastomoses, patches 50 are joined together by first component 110 at regions 122 along the blood vessel on opposite sides of the blood vessel. For other applications, the anastomosis is an end-to-side anastomosis, such as described hereinbelow with reference to FIGS. 7A-G.

Generally, arms 22 of forceps 20 are configured, e.g., have a thickness and shape, to apply sufficient pressure to the tubular structure to gently place patches 50 in good contact with the tubular structure, without applying excess pressure that might damage the tubular structure. Arms 22 are typically configured to bend when more pressure is applied than necessary, thereby preventing forceps 20 from applying excessive pressure to the tubular structure. For some applications, arms 22 are sufficiently flexible to limit a maximum amount of force applied by the patch supports 30 to the tubular structure when the patch supports are placed on opposing sides of the tubular structure and the arms are squeezed together.

For some applications, as shown in FIGS. 5 and 6, patch supports 30 are placed such that the tubular structure passes approximately along the center of patch supports 30 and patches 50. For other applications, the tubular structure is not centered, but is instead focused on an anastomosis site; for example, patch supports 30 may be positioned such that the tubular structure is positioned at approximately one third the way across of patch supports. It is noted that applicator 10 can be used in different orientations with respect to the tubular structures, as appropriate for particular surgical conditions, such a vertically, at a 45-degree angle with the tubular structure, or at a 135-degree angle with the tubular structure. Various orientations have been tested in experiments conducted by the inventors.

In some applications of the present invention, during a first stage of an application procedure, a first substance is applied to a structure in a body of a patient, such a tubular structure, such as at least one blood vessel or synthetic graft, such as manually, and/or using a syringe. During a second stage of the procedure following the first stage, applicator 10 is used to apply one or more patches 50 to the tubular structure. For some applications, patches 50 comprise a second substance, which, upon application of the patches to the tubular structure, is brought into contact with the first substance and the tubular structure.

For some applications, the first substance comprises a first component of an adhesive (i.e., a glue or sealant). For some applications, the first component comprises a viscous pre-gel, while for other applications, the first component comprises a liquid, solid, spray, or aerosol. Alternatively, the first substance does not comprise an adhesive, and may comprise a viscous pre-gel, liquid, solid, spray, or aerosol. The first substance may be provide in a container.

For some applications, the second substance comprises a second component of the adhesive, typically an adhesive curing agent, which may comprise a gel, liquid, solid, spray, or aerosol, which may be applied to one or more surfaces of patches 50 and/or be absorbed into the patches. Upon contact with the first component of the adhesive, the curing agent causes the glue to become more solid, such as a flexible solid gel, and to adhere to the tubular structure. The patch also provides mechanical support to the tubular structure. The patch is typically left on the tubular structure, and eventually biodegrades.

For some applications, such as described in above-mentioned PCT Publication WO 09/060438, the first component of the adhesive comprises a pre-gel that comprises at least one phenol-based compound, and at least one water miscible polymer. The second component of the adhesive comprises at least one cross linking agent, which may, for example, comprise calcium, capable of interacting with the at least one water miscible polymer. For some applications, each of patches 50 comprises a biodegradable thin film such as plastic, knitted mesh of fabric made from synthetic or natural polymer, or gauze prepared form oxidized cellulose. For some applications, the pre-gel further comprises non-soluble suspended solids, which may take the form of particles such as fibers. For some applications, the at least one phenol-based compound takes a form selected from monomer, non-cross linked polymer, or cross linked polymer.

Figure 7B:
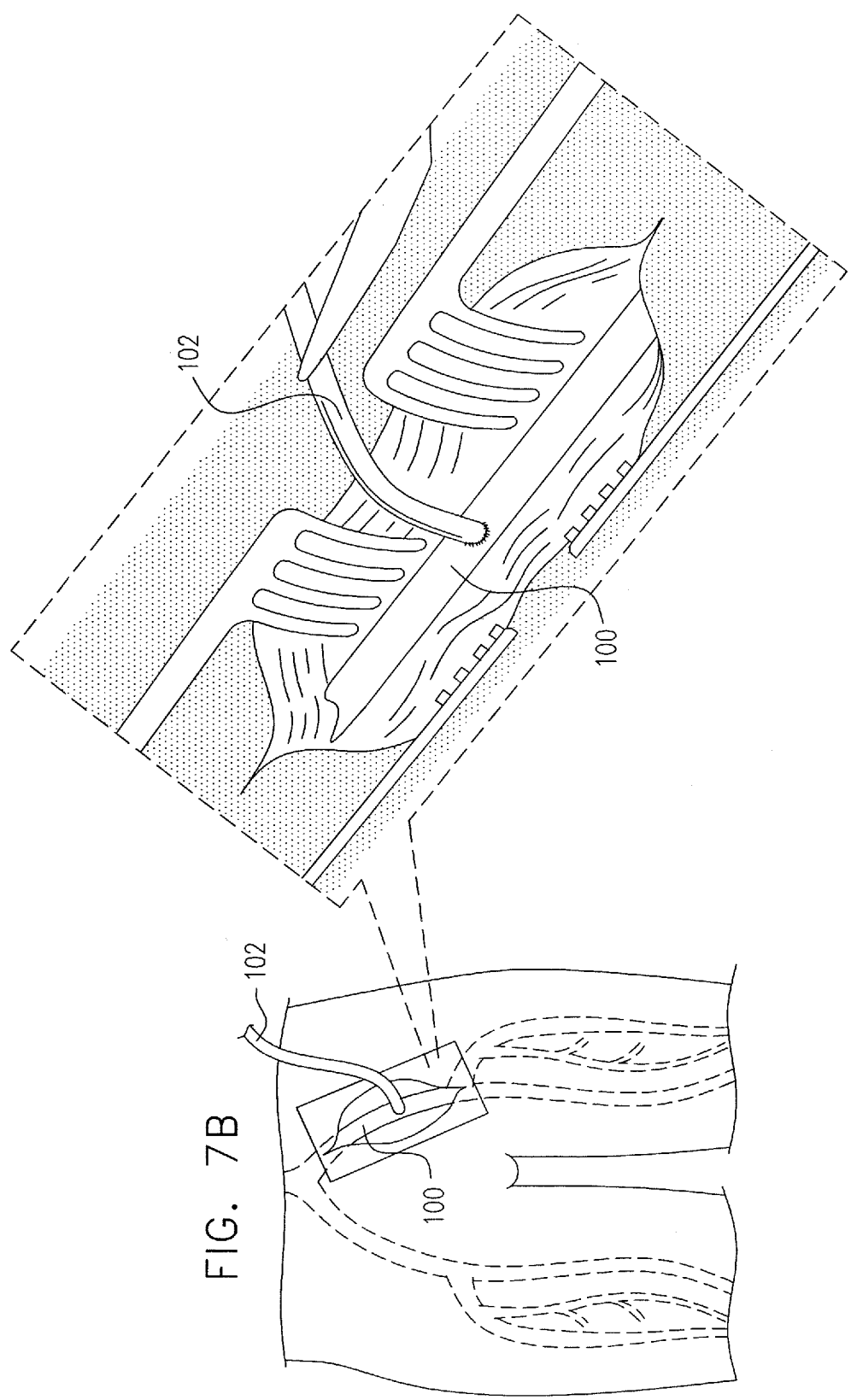

Reference is now made to FIGS. 7A-G, which are schematic illustrations of an end-to-side anastomosis procedure, performed in accordance with an application of the present invention. As shown in FIG. 7A, an incision is made and a primary blood vessel 100 is exposed. By way of example and not limitation, primary blood vessel 100 is illustrated as a femoral artery. As shown in FIG. 7B, during the anastomosis procedure, the end of a secondary tubular structure 102, such as a second blood vessel or a synthetic graft, is anastomosed to the primary blood vessel using conventional techniques, such as using sutures. For clarity of illustration, the tubular structures are shown joined at about a 90 degree angle, although in actual practice the secondary tubular structure is typically joined to the primary blood vessel at about a 45 degree angle.

During the first stage of the adhesive application procedure, first component 110 of the adhesive (e.g., a pre-gel) is applied to primary blood vessel 100 and secondary tubular structure 102 at a site 112 of the anastomosis, as shown in FIG. 7C. First component 110 may be applied from a container 114, such as a conventional syringe.

As shown in FIG. 7D, applicator 10 is positioned such that patch supports 30, including patches 50, are on opposite sides of primary blood vessel 100, and also on opposite sides of secondary tubular structure 102, in the vicinity of anastomosis site 112 at the junction between primary blood vessel 100 and secondary tubular structure 102. Arms 22 provide good accessibility to anastomosis sites even deep within the body. The surgeon can observe and control the distance between the arms and the two patches (avoiding positioning the arms too far apart, in which case the arms might touch tissue around the site, or too close together, in which case the arms might prematurely touch first component 110 of the adhesive). The surgeon can also observe and control the optimal positioning of the patches immediately over first component 110 of the adhesive. It is noted that applicator 10 can be used in different orientations with respect to the tubular structures, as appropriate for particular surgical conditions.

The surgeon squeezes arms 22 of forceps 20 toward each other, pressing patch supports 30 against and patches 50 into contact with both primary blood vessel 100 and secondary tubular structure 102, as well as first component 110 of the adhesive. The force applied by patch supports 30 to primary blood vessel 100 and secondary tubular structure 102 opens the slits, thereby releasing patches 50 from patch supports 30. The patch supports 30 are typically held against the primary blood vessel for a short period of time, such as up to about one minute, while mild pressure is applied using the forceps. During this time, the curing agent of patches cures first component 110 of the adhesive, causing patches 50 to adhere both to anastomosis site 112 and to each other at regions of the patches surrounding the site, as described hereinbelow with reference to FIG. 7F. Patches 50 are thus placed at least partially around primary blood vessel 100 at anastomosis site 112. In contrast, in conventional anastomosis procedures, after suturing the surgeon generally must apply pressure to the anastomosis site for between a few minutes and dozens of minutes (sometime up to an hour). Such extended application of pressure may be necessary because the patient has been administered a high dose of anticoagulant, or because the sutures were not well applied. Sometimes the anastomosis site is quite deep in the body, requiring the surgeon to apply the pressure with just one or two fingers for this extended period.

Applicator 10 is removed from anastomosis site 112, leaving patches 50 in place, as shown in FIG. 7F. The gentle pressure applied by yielding pads 36 of patch supports 30 generally pushes patches 50 together at regions 120 surrounding anastomosis site 112. The curing agent in the patches cures first component 110 of the adhesive at regions 120, causing the patches to stick together at regions 120, thereby forming a hermetic adhesive seal entirely around the anastomosis. Protrusions 70, if provided, generally help apply additional pressure to the patches at regions 120, to ensure good contact between the patches at these important sealing regions.

As shown in FIG. 7G, the surgeon trims excess material from the patches.

Although the procedure described above with reference to FIGS. 7A-G includes the application of two components of a dual-component adhesive, the techniques may be used mutatis mutandis to perform single-component-adhesive procedures that do not include the first component, or to perform procedures that apply one or more patches 50 without any adhesives.

In about ten experiments conducted on pigs by some of the inventors, performance of a patch applicator similar to applicator 10 described hereinabove with reference to FIGS. 1-7G was assessed. The patch applicator was used to apply patches in vivo to seal various end-to-side anastomotic suture lines, between a synthetic tubular graft and the carotid artery, and between a synthetic tubular graft and the femoral artery, using the method described hereinabove with reference to FIGS. 7A-G. In each of the anastomosis procedures, a pre-gel was applied using a syringe, and the applicator was used to apply the patches, which contained a curing agent. After the patches were brought together to press on the pre-gel, the applicator was left closed for about one minute to apply mild pressure to the pre-gel treated site. The curing agent of the patches cured the pre-gel, causing the patches to adhere to the site. When the applicator was removed from the site, the patches were left incorporated into the pre-gel on the site.

The success of the procedures was evaluated by visual inspection. In addition, the patches remained in place after the surgeon delicately touched the patches, and after the patch was trimmed in some of the procedures, as described hereinabove with reference to FIG. 7G. The success of the procedures was also evaluated functionally. Blood flow resumed upon the removal of surgical clamps from the artery (as indicated by pulsation of the artery), indicating that complete hemostasis was achieved.

Reference is now made to FIG. 8, which is a schematic illustration of an alternative configuration of applicator 10, in accordance with an application of the present invention. This configuration may be used in combination with any of the techniques described hereinabove. In this configuration, applicator 10 is configured to allow the surgeon to control the pressure in the one or more chambers 42. The surgeon may adjust the volume of gas within chambers 42 before and/or during application of the patches, in order to achieve optimal placement of the patches over the tubular structure.

Applicator 10 comprises one or more conduits 130, respective lumens of which is in fluid communication with interiors of one or more of chambers 42. For example, applicator 10 may comprises two conduits 130, which are in fluid communication with respective chambers 42 in two patch supports 30. Applicator 10 further comprises one or more control mechanisms 132, which are in fluid communication with at least one of conduits 130. For example, each of control mechanisms 132 may comprise a chamber configured to have a variable volume, such as a flexible or elastic chamber, e.g., a balloon. Applying pressure to the control mechanism chamber decreases the size of the control mechanism chamber, forcing a gas out of the control mechanism chamber and into one or more chambers 42 of patch support(s) 30 via one or more of conduits 130. For example, each of control mechanisms 132 may comprises a button 134, which, when pressed, applied pressure to the control mechanism chamber.

Applicator 10 may comprise exactly one control mechanism 132, which may be in fluid communication with a plurality of conduits 130, such as two conduits 130, which are in fluid communication with respective chambers 42 of respective patch supports 30, such as shown in FIG. 8. Alternatively, applicator 10 may comprise two control mechanisms 132, which are in fluid communication with two conduits 130, respectively, which in turn are in fluid communication with respective chambers 42 of respective patch supports 30 (configuration not shown).

For some applications, control mechanism 132 is configured to increase the pressure within at least one of chambers 42. Alternatively or additionally, control mechanism 132 may be configured to reduce the pressure within at least one chambers 42, such as by allowing gas to escape via one or more of conduits 130.

For some applications, applicator 10 is configured to monitor the time of application of patch supports 30.

For example, patch supports 30 or patches 50 may comprise a material that changes color upon interaction with first component 110.

All references to blood vessels herein should be understand by way of example and not limitation. The techniques described herein for applying patches to a blood vessel may alternatively or additionally be used to apply the patches to another structure, such as, but not limited to, an anatomical structure, such as the gastrointestinal tract (e.g., the colon), a bronchus, or the brain (such as the dura mater), or synthetic structures within a body of a patient, such as synthetic grafts (e.g., tubular synthetic grafts). Typically, but not necessarily, the structure is tubular. For some applications, the one or more patches, and, optionally, components of an adhesive, are applied to an junction between two tubular structures, such as two tubular body parts, e.g., at a site of an anastomosis between two blood vessels. The junction may, for example, be an end-to-end junction or an end-to-side junction. In the present application, including in the claims, application of the components of the adhesive and one or more patches to a blood vessel is to be understood as optionally including application of the components of the adhesive and one or more patches to a site of an anastomosis between two blood vessels.

Figure 9A:
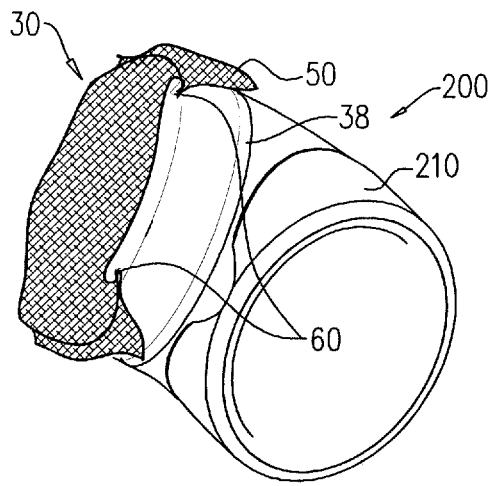
FIGS. 9A-C are schematic perspective illustrations of a finger applicator, in accordance with an application of the present invention.
Figure 9B:
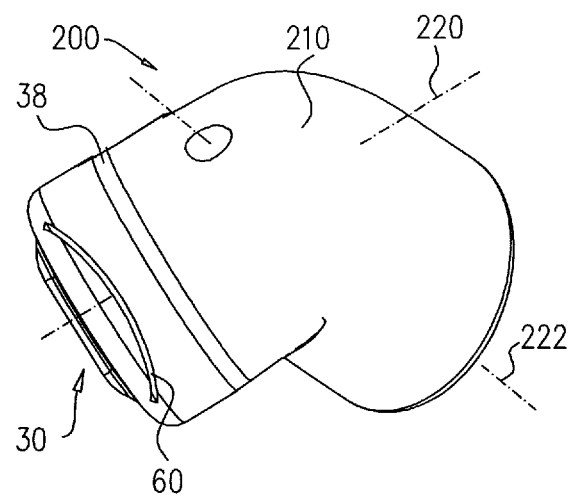

Reference is now made to FIGS. 9A-B, which are schematic perspective illustrations of a finger applicator 200, in accordance with an application of the present invention. Finger applicator 200 comprises a single patch support 30, as described hereinabove (e.g., with reference to FIGS. 2A-B and 3), and a finger-coupling element. For some applications, the finger-coupling element comprises a flexible band that is placed around the surgeon's finger.

For some applications, the finger-coupling element comprises a finger cap 210 coupled to patch support 30.

Finger cap 210 is shaped so as to define a cavity for insertion of a human finger of a surgeon, and is typically shaped like a thimble. For example, the opening of the cavity may have a diameter of at least 1 cm, less than 2.5 cm, and/or between 1 and 2.5 cm, and the length of cavity along a central longitudinal axis 222 of finger cap 210 may be at least 1 cm, less than 4 cm, and/or between 1 and 4 cm. For some applications, finger cap 210 comprises a flexible material, such as silicone. Alternatively, finger cap 210 comprises a rigid material, such as plastic or metal.

For applications in which finger cap 210 comprises a rigid material, the finger cap may serve as stiff back support structure 38, and patch support 30 does not comprise a separate stiff back support structure 38. Typically, patch support 30 is fixed to finger cap 210. Alternatively, the patch support is provided separately to the surgeon, who couples the patch support to the finger cap.

Patch 50 is removably coupled to patch support 30 such that the patch rests against the yielding pad. The yielding pad enables finger applicator 200 to gently apply the patch to the blood vessel or other tubular structure. For some applications, side surface 40 of yielding pad 36 is shaped so as to define one or more slits 60, as described hereinabove.

For some applications, patch support 30 extends laterally from finger cap 210. For example, a line 220 normal to the surface of patch support 30 may form an angle of between 60 and 120 degrees, e.g., 90 degrees, with central longitudinal axis 222 of finger cap 210.

Figure 9C:
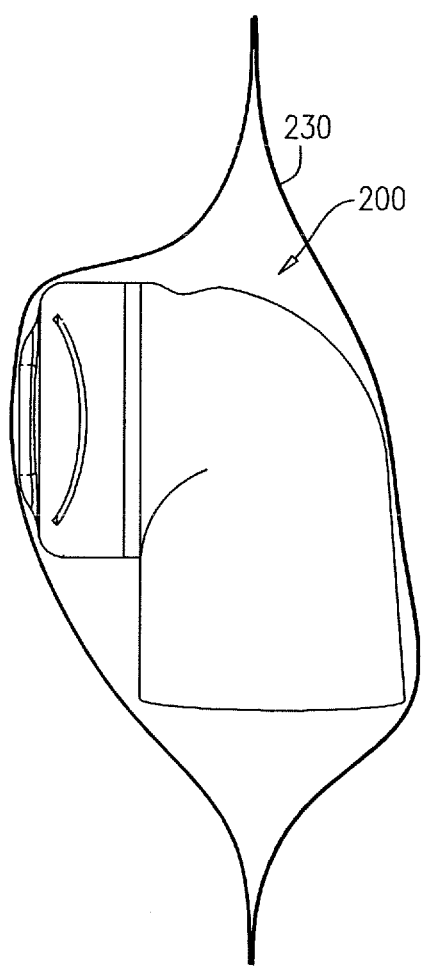

Reference is made to FIG. 9C, which is a schematic illustration of packaging of finger applicator 200, in accordance with an application of the present invention. In this application, finger applicator 200 is packaged in protective covering 230, with patch 50 removably coupled to patch support 30. For some applications, a kit is provided that comprises one or more packaged finger applicators 200 and a container. The container contains a first component of an adhesive and not a second component of the adhesive; for example, the first component may comprise a viscous pre-gel. Patch 50 comprises the second component of the adhesive and not the first component of the adhesive.

The scope of the present invention includes embodiments described in the following applications, which are assigned to the assignee of the present application and are incorporated herein by reference. For some applications, techniques and apparatus described in one or more of the following applications are combined with techniques and apparatus described herein:

International Application PCT/IL2008/001451, filed Nov. 5, 2008, entitled, "Adhering bandage and methods of applying the same," which published as PCT Publication WO 09/060438;

International Application PCT/IL2008/001452, filed Nov. 5, 2008, entitled, "Adhesives and methods of applying the same," which published as PCT Publication WO 09/060439;

International Application PCT/IL2006/000289, filed Mar. 2, 2006, which published as PCT Publication WO 06/092798, and U.S. application Ser. No. 11/885,555, which published as US Patent Application Publication 2008/0167400, in the national stage thereof;

U.S. Provisional Patent Application 61/202,688, filed Mar. 27, 2009;

U.S. Provisional Patent Application 61/182,771, filed Jun. 1, 2009;

U.S. Provisional Patent Application 61/186,911, filed Jun. 15, 2009;

International Application PCT/IL2010/000268, filed Mar. 28, 2010, which published as PCT Publication WO 2010/109471;

International Application PCT/IL2010/000431, filed Jun. 1, 2010, which published as PCT Publication WO 2010/140146; and International Application PCT/IL2010/000471, filed Jun. 15, 2010, which published as PCT Publication WO 2010/146582.

For some applications, the methods and applicators described herein are used, mutatis mutandis, to apply materials other than adhesive glues or curing agents.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for applying one or more patches to a tubular structure in a body of a patient, the apparatus comprising an applicator, which is configured to removably hold the one or more patches, and to place the one or more patches at least partially around the tubular structure, wherein the applicator comprises one or more patch supports, and wherein each of the patch supports comprises:
   a yielding pad, which is removably coupleable to one of the patches; and
   a stiff back support structure, to which the yielding pad is fixed,
   wherein each of the patch supports is shaped so as to define at least one chamber that itself has a volume of at least 0.5 ml when the patch supports are in respective resting states, and
   wherein the applicator is characterized by at least one feature selected from the group of features consisting of:
   (a) the at least one chamber of each of the patch supports is filled with a gas or a gel, and is sealed such that the gas or the gel cannot escape from the chamber, and
   (b) the at least one chamber of each of the patch supports is filled with a gas, which compresses when the at least one chamber is squeezed upon applying the patch support thereof to the tubular structure.

2. The apparatus according to claim 1, wherein each of the patch supports is shaped so as to define the at least one chamber thereof between the yielding pad thereof and the back support structure thereof.

3. The apparatus according to claim 1, wherein each of the patch supports is shaped so as to define the at least one chamber thereof entirely within the yielding pad thereof.

4. The apparatus according to claim 1, wherein the yielding pad of each of the patch supports is shaped so as to define:
   a front surface that faces away from the back support structure thereof, and
   a side surface between the front surface and the back support structure thereof, wherein the side surface is shaped so as to define one or more slits extending within the yielding pad, and wherein the slits are configured to removably couple the one of the patches to the yielding pad.

5. The apparatus according to claim 4, wherein the yielding pad is shaped such that pressing the front surface against the tubular structure opens the slits, thereby releasing the one of the patches from the yielding pad.

6. The apparatus according to claim 4, wherein the side surface is shaped so as to define exactly two slits on opposite sides of the yielding pad.

7. The apparatus according to claim 4, wherein at least one of the slits is arcuate at least when in a closed position.

8. The apparatus according to claim 1,
   wherein the applicator comprises a forceps, which comprises exactly two arms,
   wherein the one or more patch supports comprise exactly two patch supports, which are coupled to the two arms, respectively,
   wherein the patch supports comprise exactly two yielding pads, respectively,
   wherein the arms and the patch supports are configured such that front surfaces defined by the yielding pads, respectively, face each other, and
   wherein the arms are sufficiently flexible to limit a maximum amount of force applied by the patch supports to the tubular structure when the patch supports are placed on opposing sides of the tubular structure and the arms are squeezed together.

9. The apparatus according to claim 1, wherein the yielding pad of each of the patch supports is shaped so as to define a front surface that faces away from the back support structure thereof, and wherein each of the patch supports is configured such that, when pressed against the tubular structure, central and peripheral portions of the front surface apply different respective forces to the tubular structure.

10. The apparatus according to claim 1, wherein the volume of the at least one chamber of each of the patch supports is at least 1 ml when the patch supports are in their respective resting states.

11. The apparatus according to claim 1, wherein at least one of the patch supports is shaped so as to define exactly one chamber.

12. The apparatus according to claim 1, wherein at least one of the patch supports is shaped so as to define a plurality of chambers, each of which has a volume of at least 0.5 ml.

13. The apparatus according to claim 1, wherein the at least one chamber of each of the patch supports is filled with the gas or the gel, and is sealed such that the gas or the gel cannot escape from the chamber.

14. The apparatus according to claim 13, wherein the at least one chamber of each of the patch supports is filled with the gel.

15. The apparatus according to claim 13, wherein the at least one chamber of each of the patch supports is filled with the gas.

16. The apparatus according to claim 1, wherein the at least one chamber of each of the patch supports is filled with the gas, which compresses when the at least one chamber is squeezed upon applying the patch support thereof to the tubular structure.

17. The apparatus according to claim 16, wherein the applicator comprises one or more control mechanisms, which (a) are in fluid communication with the at least one chamber, and (b) are configured to control a pressure in the at least one chamber.

18. The apparatus according to claim 17,
wherein the applicator further comprises one or more conduits, respective lumens of which are in fluid communication with respective interiors of the at one chamber, and
wherein the one or more control mechanisms are in fluid communication with at least one of the conduits.

19. Apparatus for applying one or more patches to a tubular structure in a body of a patient, the apparatus comprising an applicator, which is configured to removably hold the one or more patches, and to place the one or more patches at least partially around the tubular structure, wherein the applicator comprises one or more patch supports, and wherein each of the patch supports comprises:
 a yielding pad, which is removably coupleable to one of the patches; and
 a stiff back support structure, to which the yielding pad is fixed,
 wherein each of the patch supports is shaped so as to define at least one chamber that itself has a volume of at least 0.5 ml when the patch supports are in respective resting states, and
 wherein the yielding pad of each of the patch supports (a) is shaped so as to define a front surface that faces away from the back support structure thereof, and (b) is shaped such that a central portion of the front surface, but not the entire front surface, defines a protrusion that protrudes from the front surface in a direction away from the back support structure, at least when no force is applied to the front surface.

20. Apparatus for applying one or more patches to a tubular structure in a body of a patient, the apparatus comprising an applicator, which is configured to removably hold the one or more patches, and to place the one or more patches at least partially around the tubular structure, wherein the applicator comprises one or more patch supports, and wherein each of the patch supports comprises:
 a stiff back support structure; and
 a yielding pad, which is fixed to the back support structure, and which is shaped so as to define:
  a front surface that faces away from the back support structure, and
  a side surface between the front surface and the back support structure, wherein the side surface is shaped so as to define one or more slits extending within the yielding pad, and wherein the slits are configured to removably couple one of the patches to the yielding pad.

21. The apparatus according to claim 20, wherein the yielding pad is shaped such that pressing the front surface against the tubular structure opens the slits, thereby releasing the one of the patches from the yielding pad.

22. The apparatus according to claim 20, wherein the side surface is shaped so as to define exactly two slits on opposite sides of the yielding pad.

23. The apparatus according to claim 20, wherein at least one of the slits is arcuate at least when in a closed position.

24. The apparatus according to claim 23, wherein ends of the at least one of the slits are closer to the front surface than to the back support structure, at least when the at least one of the slits is in the closed position.

25. A method for applying one or more patches to a tubular structure in a body of a patient, the method comprising:
 providing an applicator, which is configured to removably hold the one or more patches, and which includes one or more patch supports, wherein each of the patch supports includes (a) a yielding pad, to which one of the patches is removably coupled, and (b) a stiff back support structure, to which the yielding pad is fixed, wherein each of the patch supports is shaped so as to define at least one chamber that itself has a volume of at least 0.5 ml when the patch supports are in their respective resting states, and wherein the applicator is characterized by at least one feature selected from the group of features consisting of: (a) the at least one chamber of each of the patch supports is filled with a gas or a gel, and is sealed such that the gas or the gel cannot escape from the chamber, and (b) the at least one chamber of each of the patch supports is filled with a gas, which compresses when the at least one chamber is squeezed upon applying the patch support thereof to the tubular structure; and
 placing the one or more patches at least partially around the tubular structure, by using the applicator to press the one or more patch supports against the tubular structure.

26. The method according to claim 25,
wherein providing the applicator comprises providing the applicator in which the yielding pad of each of the patch supports is shaped so as to define (a) a front surface that faces away from the back support structure thereof, and (b) a side surface between the front surface and the back support structure thereof, wherein the side surface is shaped so as to define one or more slits extending within the yielding pad, and wherein the slits are configured to removably couple the one of the patches to the yielding pad, and
wherein placing comprises pressing the front surface against the tubular structure so as to open the slits, thereby releasing the one of the patches from the yielding pad.

27. The method according to claim 25, further comprising, after placing, releasing the one or more patches from the patch supports.

28. The method according to claim 25, wherein placing comprises placing the one or more patches entirely around the tubular structure.

29. The method according to claim 25, wherein the tubular structure is a blood vessel to which a structure has been anastomosed at an anastomosis site, the structure selected from the group selected from: a synthetic graft and a second blood vessel, and wherein placing comprises placing the one or more patches at least partially around the tubular structure and the anastomosis site.

30. The method according to claim 25, wherein the tubular structure is a blood vessel upon which an end-to-end anastomosis has been performed at an anastomosis site, and wherein placing comprises placing the one or more patches at least partially around the tubular structure at the anastomosis site.

31. A method for applying one or more patches to a tubular structure in a body of a patient, the method comprising:

provifing an applicator, which is configured to removably hold the one or more patches, and which includes one or more patch supports, wherein each of the patch supports includes (a) a stiff back support structure, and (b) a yielding pad, which is fixed to the back support structure, and which is shaped so as to define (i) a front surface that faces away from the back support structure, and (ii) a side surface between the front surface and the back support structure, wherein the side surface is shaped so as to define one or more slits extending within the yielding pad, and wherein the slits are configured to removably couple the one of the patches to the yielding pad; and placing the one or more patches at least partially around the tubular structure, by using the applicator to press the one or more patch supports against the tubular structure, so as to open the slits, thereby releasing the one of the patches from the yielding pad.

32. The method according to claim 31, wherein placing comprises placing the one or more patches entirely around the tubular structure.

33. The method according to claim 31, wherein the tubular structure is a blood vessel to which a structure has been anastomosed at an anastomosis site, the structure selected from the group selected from: a synthetic graft and a second blood vessel, and wherein placing comprises placing the one or more patches at least partially around the tubular structure and the anastomosis site.

34. The method according to claim 31, wherein the tubular structure is a blood vessel upon which an end-to-end anastomosis has been performed at an anastomosis site, and wherein placing comprises placing the one or more patches at least partially around the tubular structure at the anastomosis site.

* * * * *